United States Patent
Kaetzel et al.

(10) Patent No.: US 10,525,103 B2
(45) Date of Patent: *Jan. 7, 2020

(54) COMBINED USE OF A VECTOR ENCODING A MODIFIED RECEPTOR AND ITS EXOGENOUS AGONIST IN THE TREATMENT OF SEIZURES

(71) Applicant: UCL BUSINESS LTD, London (GB)

(72) Inventors: Dennis Kaetzel, London (GB); Matthew Charles Walker, London (GB); Stephanie Schorge, London (GB); Dimitri Michael Kullmann, London (GB)

(73) Assignee: UCL BUSINESS LTD, London (GB)

(*) Notice: Subject to any disclaimer, the term of this patent is extended or adjusted under 35 U.S.C. 154(b) by 0 days.

This patent is subject to a terminal disclaimer.

(21) Appl. No.: 16/247,133

(22) Filed: Jan. 14, 2019

(65) Prior Publication Data
US 2019/0134155 A1     May 9, 2019

Related U.S. Application Data

(63) Continuation of application No. 15/125,762, filed as application No. PCT/GB2015/050657 on Mar. 6, 2015, now Pat. No. 10,391,145.

(30) Foreign Application Priority Data

Mar. 13, 2014    (GB) .................................. 1404470.5

(51) Int. Cl.
| | |
|---|---|
| *A61K 38/17* | (2006.01) |
| *A61K 31/5513* | (2006.01) |
| *A61K 9/00* | (2006.01) |
| *A61K 31/55* | (2006.01) |
| *A61K 48/00* | (2006.01) |
| *C07K 14/705* | (2006.01) |
| *C12N 7/00* | (2006.01) |
| *C12N 15/86* | (2006.01) |

(52) U.S. Cl.
CPC ........ *A61K 38/1787* (2013.01); *A61K 9/0019* (2013.01); *A61K 31/55* (2013.01); *A61K 31/5513* (2013.01); *A61K 48/0058* (2013.01); *A61K 48/0075* (2013.01); *C07K 14/70571* (2013.01); *C12N 7/00* (2013.01); *C12N 15/86* (2013.01); *C12N 2710/16043* (2013.01); *C12N 2740/15043* (2013.01); *C12N 2750/14143* (2013.01)

(58) Field of Classification Search
CPC .. A61K 9/0019; A61K 31/5513; A61K 31/55; A61K 38/1787; A61K 48/0058; A61K 48/0075; C07K 14/70571; C12N 15/86; C12N 2750/14143; C12N 7/00; C12N 2740/16043; C12N 2740/15043
See application file for complete search history.

(56) References Cited

FOREIGN PATENT DOCUMENTS

| WO | 97/35478 A1 | 10/1997 |
|---|---|---|
| WO | 0018903 A2 | 4/2000 |
| WO | 2016/161124 A1 | 10/2016 |

OTHER PUBLICATIONS

Alexander et al., "Remote Control of Neuronal Activity in Transgenic Mice Expressing Evolved G Protein-Coupled Receptors", Neuron 63:27-39 (2009).
Armbruster et al., "Evolving the lock to fit the key to create a family of G protein-coupled receptors potently activated by an inert ligand", PNAS 104(12):5163-5168 (2007).
Cook et al., "Prediction of seizure likelihood with a long-term, implanted seizure advisory system in patients with drug-resistant epilepsy: a first-in-man study", Lancet Neurol. 12:563-571 (2013).
Farrell et al., "Pharmacosynthetics: Reimagining the pharmacogenetic approach", Brain Research 1511:6-20 (2013).
Ferguson et al., "Transient neuronal inhibition reveals opposing roles of indirect and direct pathways in sensitization", Nature Neuroscience 14(1):22-24 (2011).
Kätzel et al., "Chemical—genetic attenuation of focal neocortical seizures", Nature Communications 5:3847 (2014). (9 pages).
Kreitzer et al., "Investigating Striatal Function Through Cell-Type-Specific Manipulations", Neuroscience 198:19-26 (2011).
Krook-Magnuson et al., "On-demand optogenetic control of spontaneous seizures in temporal lobe epilepsy", Nature Communications 4:1376 (2013). (8 pages).
Majeed et al., "5-HT stimulation of heart rate in *Drosophila* does not act through cAMP as revealed by pharmacogenetics", Journal of Applied Physiology 115:1656-1665 (2013).
Paz et al., "Closed-loop optogenetic control of thalamus as a new tool to interrupt seizures after cortical injury", Nature Neuroscience 16(1):64-70 (2013).
Wykes et al., "Optogenetic and Potassium Channel Gene Therapy in a Rodent Model of Focal Neocortical Epilepsy", Science Translational Medicine 4(161):161ra152 (2012). (11 pages).
Heeroma et al., "Episodic ataxia type 1 mutations differentially affect neuronal excitability and transmitter release", Dis Model Mech 2(11-12) 612-619 (2009).

(Continued)

*Primary Examiner* — Gregory S Emch
(74) *Attorney, Agent, or Firm* — Nixon Peabody LLP; Mark J. FitzGerald; Teresa A. Ptashka

(57) ABSTRACT

The invention provides methods and materials for treating a seizure disorder such as epilepsy in a patient which employ a vector encoding a modified receptor, the so-called "DREADD" receptor being characterised by (i) a decreased responsiveness to its endogenous activating ligand (ii) a retained or enhanced responsiveness to an exogenous agonist. The modified receptor is expressed in neurons of a seizure focus in brain of the patient, and an exogenous agonist is administered which activates the modified receptor to reversibly alters the excitability of the neurons in the seizure focus leading to synaptic silencing or other inhibition.

4 Claims, 5 Drawing Sheets

Figure 1:
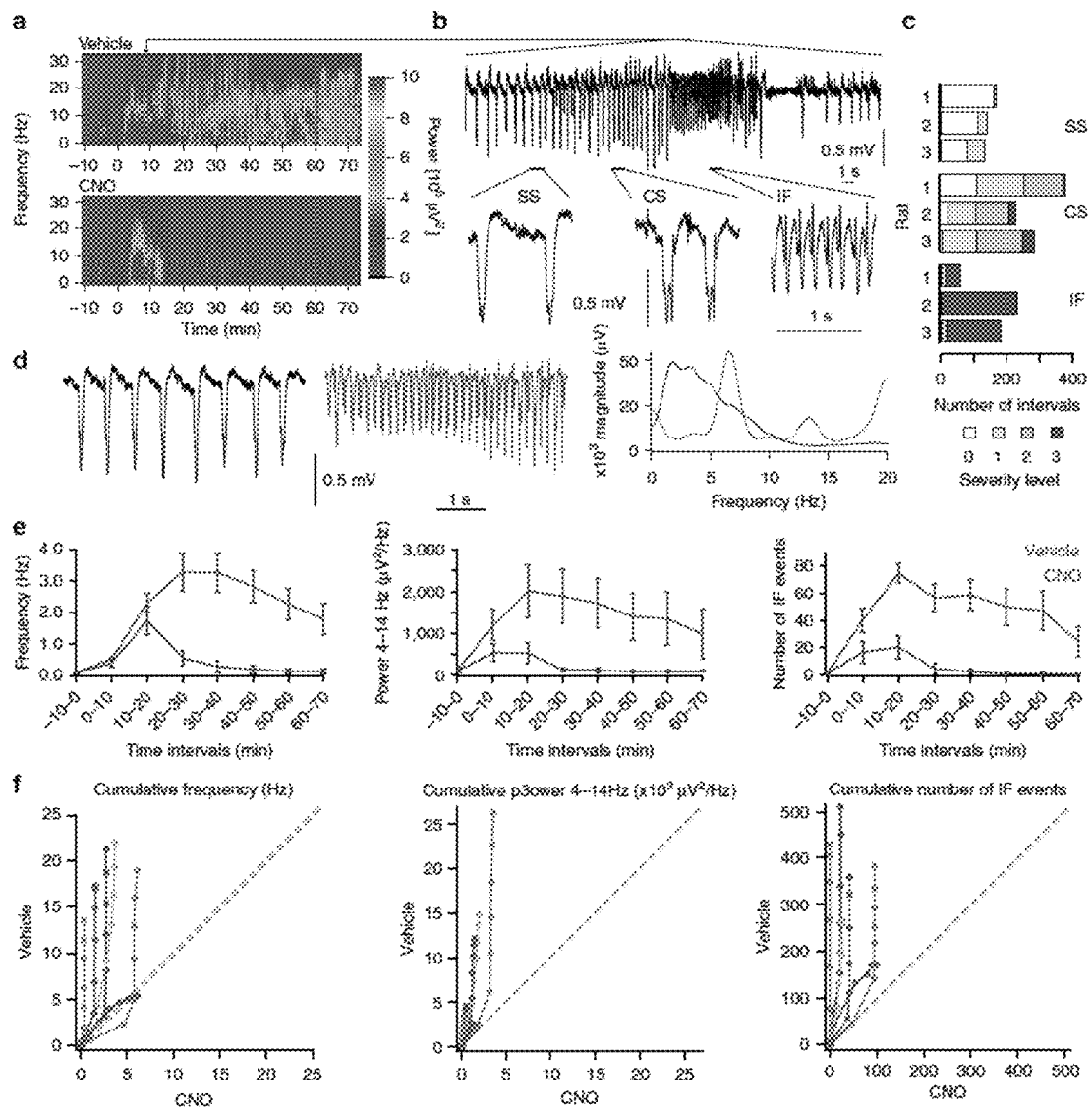

Specification includes a Sequence Listing.

(56) References Cited

OTHER PUBLICATIONS

Akam et al., "Oscillatory dynamics in the hippocampus support dentate gyrus—CA3 coupling", Nat Neurosci 15(5) 763-768 (2012).
Nawaratne et al., "New insights into the function of M4 muscarinic acetylcholine receptors gained using a novel allosteric modulator and a DREADD (designer receptor exclusively activated by a designer drug)", Mol Pharmacol 74(4) 1119-1131 (2008).
Pei et al., "Engineered GPCRs as tools to modulate signal transduction", Physiology (Bethesda) 23; 313-321 (2008).
Wulff et al., "Chemical genetics: receptor-ligand pairs for rapid manipulation of neuronal activity", Curr Opin Neurobiol 22(1) 54-60 (2012).
Louis et al., "Chronic focal epilepsy induced by microinjection of tetanus toxin into the cat motor cortex", Electroencephalogr. Clin. Neurophysiol. 75:548-557 (1990).
Nilsen et al., "Characterization of the tetanus toxin model of refractory focal neocortical epilepsy in the rat", Epilepsia 46(2) 179-187 (2005).
Cockerell et al., "Clinical and physiological features of epilepsia partialis continua. Cases ascertained in the UK", Brain 119(Pt 2) 393-407 (1996).
Garner et al., "Generation of a synthetic memory trace", Science 335(6075) 1513-1516 (2012).
Chen et al., "The first structure-activity relationship studies for designer receptors exclusively activated by designer drugs", ACS Chem Neurosci 6(3) 476-484 (201.
UK Search Report for Appl. No. GB1404470.5 dated Dec. 8, 2014.
Amorim et al., "Effects of Al receptor agonist/antagonist on spontaneous seizures in pilocarpine-induced epileptic rats", Epilepsey Behavo 61; 168-173 (2016).
Carmignoto et al., "Astrocyte calcium signaling and epilepsy", Glia 60(8) 1227-1233 (2012).
Choe et al., "Potassium channel structures", Nat Rev Neurosci 3(2) 115-121 (2002).
Cortez et al., "Infantile spasms and Down syndrome: a new animal model", Pediatr Re 65(5) 499-503 (2009).
During et al., "Adenosine: a potential mediator of seizure arrest and postictal refractoriness", Ann Neurol 32(5) 618-624 (1992).
Gajada et al., "Involvement of gap junctions in the manifestation and control of the duration of seizures in rats in vivo", Epilepsia 44(12) 1596-1600 (2003).
Gloyn et al., "Activating mutations in the gene encoding the ATP-sensitive potassium-channel subunit Kir6.2 and permanent neonatal diabetes", N Engl J Med 350(18) 1838-1849 (2004).
Huberfeld et al., "Perturbed chloride homeostasis and GABAergic signaling in human temporal lobe epilepsy", J Neurosci 27(37) 9866-9873 (2007).
Kobayashi et al., "Inhibitory effects of the antiepileptic drug ethosuximide on G protein-activated inwardly rectifying K+ channels", Neuropharmacology 56(2) 499-506 (2009).
Snead et al., "Evidence for GABAB-mediated mechanisms in experimental generalized absence seizures", Eur J Pharmacol 213(3) 343-349 (1992).
Staley et al., "Ionic mechanisms of neuronal excitation by inhibitory GABAA receptors", Science 269(5226) 977-981 (1995).
Swiader et al., "Modulation of adenosinergic system and its application for the treatment of epilepsy", Pharmacol Rep 66(3) 335-342 (2014).
Trevelyan et al., "How inhibition influences seizure propagation", Neuropharmacology 69; 45-54 (2013).
Turrigiano et al., "Homeostatic synaptic plasticity: local and global mechanisms for stabilizing neuronal function", Cold Spring Harb Persepect Biol 4(1) a005736 (2012).
Venzi et al., "A critical evaluation of the gamma-hydroxybutyrate (GHB) model of absence seizures", CNS Neurosci Ther 21(2) 123-140 (2015).
Voipio et al., "GABAergic excitation and K(+)—mediated volume transmission in the hippocampus", Prog Brain Res 125: 329-338 (2000).
Wu et al., "Transgenic mice over-expressing GABA(B)R1a receptors acquire an atypical absence epilepsy-like phenotype", Neurobiol Dis 26(2) 439-451 (2007).
Yu et al., "Spontaneous neural activity is required for the establishment and maintenance of the olfactory sensory map", Neuron 42(4) 553-566 (2004).
Zhang et al., "Propagation of epileptiform activity can be independent of synaptic transmission, gap junctions, or diffusion and is consistent with electrical field transmission", J Neurosci 34(4) 1409-1419 (2014).

COMBINED USE OF A VECTOR ENCODING A MODIFIED RECEPTOR AND ITS EXOGENOUS AGONIST IN THE TREATMENT OF SEIZURES

CROSS-REFERENCE TO RELATED APPLICATIONS

This application is a continuation application of U.S. application Ser. No. 15/125,762 filed Apr. 6, 2017 which claims benefit under 35 U.S.C. § 371 National Phase Entry Application of International Application No. PCT/GB2015/050657 filed Mar. 6, 2015, which designates the U.S. and which claims priority to GB Application No. 1404470.5 filed Mar. 13, 2014, the contents of each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Sep. 8, 2016, is named 7100985.TXT and is 10,841 bytes in size.

TECHNICAL FIELD

The present invention relates generally to genetic-therapy based methods and materials for use in treating epilepsy and similar neurological disorders.

BACKGROUND ART

Epilepsy is defined by recurrent episodes of seizures, which are brief involuntary behavioral alterations caused by paroxysmal intense electrical discharges in the brain.

Epilepsy affects up to 1% of the population (over 50 million people) (1) and is resistant to drug therapy in at least 20% of cases (2). It represents a serious burden to society and to affected individuals. Even with the best current treatments, over 25% of patients continue to have seizures which are seriously disruptive to their lives.

Epilepsy can be focal (arising from a specific brain area) or generalised (arising from both hemispheres). People with focal-onset epilepsy are especially prone to pharmacoresistance (3). The epileptogenic zone in such cases is often restricted to a small region that can often be localized with imaging and electrophysiological techniques (4). However, surgical removal of the seizure focus can successfully treat only about 5% of pharmacoresistant patients, and is often inappropriate in focal neocortical epilepsy because of proximity to eloquent cortex (5, 6).

WO00/18903 describes a system for therapy of epilepsy and intractable pain, as well as for cardiac arrhythmias, in which so-called "electrical silencing" genes are transferred into cells with sensitive control of the transgene expression. Examples given are an ecdysone-inducible promoter which drives the expression inwardly rectifying potassium channels in polycistronic adenoviral vectors. It is reported that while normal electrical activity is not affected, after the induction of gene expression excitability is suppressed.

Furthermore gene therapy targeted to the epileptogenic zone has been shown to be effective in rodent models of epilepsy including focal neocortical epilepsy (7).

However, viral delivery of transgenes that alter excitability permanently may impair essential function of circuits near the seizure focus. An attractive strategy would be to suppress circuit excitability 'on demand' upon detection of a seizure. Recently progress in optogenetic seizure suppression in rodents has shown that this is, in principle, feasible (7-9). One of the main limitations to clinical translation is the need to deliver light of the appropriate wavelength, intensity and duration to the region of transduced neurons. This necessitates the implantation of optical devices and suffers from the strong attenuation of light in brain tissue.

It can thus be seen that novel methods of treating epilepsy, such as focal epilepsy, would provide a contribution to the art.

DISCLOSURE OF THE INVENTION

The present inventors have developed a novel therapeutic system that uses vectors to express a modified receptor that can alter the excitability of a restricted subset of neurons in the seizure focus, but where the receptor is activated only when a specific exogenous ligand is also administered.

The receptor that has been mutated to render it insensitive to endogenous neurotransmitters but sensitive to a substance that normally has no effect on brain function.

Receptors modified in this way are known per se (10, 11, 24 for example) and have been called DREADDs (Designer Receptors Exclusively Activated by Designer Drugs) and RASSLs (Receptors Activated Solely by Synthetic Ligands) in the literature. However such modified receptors have not previously been suggested for use in the treatment of epilepsy. Some of the technology described herein was published after the presently claimed priority date (26).

By way of example, the inventors have demonstrated that expressing an inhibitory DREADD GPCR, referred to as hM4Di, in an in vivo model of focal epilepsy is able to reduce seizures when a specific ligand CNO (clozapine-N-oxide) is administered systemically. They tested this in two models of acute seizures and also in a model of chronic pharmaco-resistant epilepsy, and applied several complementary methods to analyse electrical activity in the brain (electroencephalogram—EEG). The treatment was well tolerated and seizures were suppressed only for the duration that CNO was present in the brain, approximately 45-60 minutes following a single intraperitoneal injection.

The treatments of the invention can be targeted both to the brain region where the viral vector is injected and to the cell type within that region and so the effect when the ligand is delivered can be effectively localised, and in the absence the ligand there would not be expected to be any effect on brain function.

Thus the therapy is both targeted and temporally limited. The preclinical model of epilepsy used in the Examples herein is one that does not respond to systemic drugs suggesting that the invention can have utility in patients who are not currently effectively treated.

Thus in one aspect of the invention there is provided a method of treating a seizure disorder in a patient suffering from said disorder, which method comprises:
(a) administering to said patient a vector encoding a modified receptor, the modified receptor being characterised by (i) a decreased responsiveness to its endogenous activating ligand (ii) a retained or enhanced responsiveness to an exogenous agonist,
wherein said modified receptor is expressed neurons of a seizure focus in brain of the patient;
(b) administering to said patient said exogenous agonist, whereby the presence of said agonist in the brain of the patient activates said modified receptor, whereby activation of said modified receptor reversibly alters, preferably inhibits, the excitability of the neurons in the seizure focus.

In another aspect there is provided a method for selectively inhibiting the excitability of e.g. excitatory neurons in the brain of a mammal in a region- and time-specific manner, the method comprising the steps of:
(a) administering to said mammal a vector encoding a modified receptor, the modified receptor being characterised by (i) a decreased responsiveness to its endogenous activating ligand (ii) a retained or enhanced responsiveness to an exogenous agonist,
wherein said modified receptor is expressed in said neurons in the brain of the mammal;
(b) administering to said mammal said exogenous agonist, whereby the presence of said agonist in the brain of the patient activates said modified receptor,
whereby activation of said modified receptor inhibits the excitability of the neurons.

In other embodiments activation of an excitatory receptor may lead to activation of inhibitory neurons, leading again to an inhibitory response such as synaptic silencing or inhibition.

The mammal may be a non-human mammal e.g. a test animal such as a rodent (e.g. mouse, rat) or primate. The mammal may be a transgenic mammal. Such test animals form further aspects of the invention.

In related aspects the patient or mammal may have been previously administered a vector, prior to performance of the method.

The invention also provides a vector encoding a modified receptor, and an exogenous agonist for said receptor, for use in a method of treatment of a seizure disorder in a patient suffering from said disorder, which treatment comprises:
(a) administering to said patient said vector, wherein the modified receptor is characterised by (i) a decreased responsiveness to its endogenous activating ligand (ii) a retained or enhanced responsiveness to the exogenous agonist,
wherein said modified receptor is expressed neurons of a seizure focus in brain of the patient;
(b) administering to said patient said exogenous agonist, whereby the presence of said agonist in the brain of the patient activates said modified receptor,
whereby activation of said modified receptor reversibly alters the excitability of the neurons in the seizure focus.

The invention also provides a vector encoding a modified receptor for use in a method of treatment of a seizure disorder in a patient suffering from said disorder, which treatment comprises:
(a) administering to said patient said vector, wherein the modified receptor is characterised by (i) a decreased responsiveness to its endogenous activating ligand (ii) a retained or enhanced responsiveness to an exogenous agonist,
wherein said modified receptor is expressed neurons of a seizure focus in brain of the patient;
(b) administering to said patient said exogenous agonist, whereby the presence of said agonist in the brain of the patient activates said modified receptor,
whereby activation of said modified receptor reversibly alters the excitability of the neurons in the seizure focus.

The invention also provides an exogenous agonist for use in a method of treatment of a seizure disorder in a patient suffering from said disorder, which treatment comprises:
(a) administering to said patient a vector encoding a modified receptor, the modified receptor being characterised by (i) a decreased responsiveness to its endogenous activating ligand (ii) a retained or enhanced responsiveness to an exogenous agonist,
wherein said modified receptor is expressed neurons of a seizure focus in brain of the patient;
(b) administering to said patient said exogenous agonist, whereby the presence of said agonist in the brain of the patient activates said modified receptor,
whereby activation of said modified receptor reversibly alters the excitability of the neurons in the seizure focus.

The invention also provides an exogenous agonist for use in a method of treatment of a seizure disorder in a patient suffering from said disorder,
wherein said patient has previously been administered a vector encoding a modified receptor, the modified receptor being characterised by (i) a decreased responsiveness to its endogenous activating ligand (ii) a retained or enhanced responsiveness to the exogenous agonist,
wherein said modified receptor is expressed neurons of a seizure focus in brain of the patient;
which treatment comprises administering to said patient said exogenous agonist,
whereby the presence of said agonist in the brain of the patient activates said modified receptor,
whereby activation of said modified receptor reversibly alters the excitability of the neurons in the seizure focus The methods of treatment or therapy are described in more detail hereinafter.

The invention also provides a use of a vector and\or agonist as defined herein in the preparation of a medicament for use in a method of treatment or therapy as described herein.

Some particular aspects of the invention will now be discussed in more detail:

Receptors

As noted above receptors modified to be solely activated by artificial agonists have been known in the art for many years, and are sometimes termed DREADDs or RASSLs.

Those skilled in the art can provide such receptors using known methods and, in the light of the present disclosure, apply them in the present invention. The terms "modified receptor" or the like, DREADD and RASSL are used interchangeably herein, unless context demands otherwise.

For example WO97/35478 describes the preparation of RASSLs. The content of that application, in respect of its description of the preparation and characteristics of RASSLs is specifically incorporated herein by reference. WO97/35478 teaches how RASSLs may be prepared from G protein-coupled receptors, including Gi coupled acetylcholine muscarinic receptors. The content includes a description of the "Construction of RASSLs" pages 20-30 of WO97/35478. Additionally certain definitions relating to RASSLs from WO97/35478 are used herein for consistency with their art-recognised sense. A RASSL as described therein is a modified G protein-coupled receptor having decreased binding affinity for a selected natural (i. e. endogenous) ligand of the GPCR (relative to binding of the selected ligand by a wild-type G protein-coupled receptor), but having normal, near normal, or preferably enhanced binding affinity for an exogenous, typically synthetic, small molecule. Thus, RASSL-mediated activation of RASSL-expressing cells does not occur to a significant extent in vivo in the presence of the natural ligand, but responds significantly upon exposure to an exogenously introduced small molecule. Put another way the RASSL is superiorly activated by the exogenous ligand as compared to the natural ligand (i.e., activated to a greater or more significant extent by binding of the small molecule ligand than by binding to a selected natural ligand at a similar concentration).

GPCRs

Preferred receptors for use in the present invention are modified G protein-coupled receptors (GPCRs) which bind synthetic small molecules not normally present in the brain.

The methods described herein may have the purpose of affecting or eliciting G protein-mediated cellular response of a eukaryotic cell, particularly in a neuron in the brain of a mammal. The neuron will typically be a neuronal cell within a neural population which has been transformed with the vector encoding the modified GPCR.

"G protein-coupled receptor" as used herein means a receptor that, upon binding of its natural ligand and activation of the receptor, transduces a G protein-mediated signal(s) that results in a cellular response. G protein-coupled receptors form a large family of evolutionarily related proteins (see WO97/35478). Proteins that are members of the G protein-coupled receptor family are generally composed of seven putative transmembrane domains. G protein coupled receptors were also known in the art as "seven transmembrane segment (7TM) receptors" and as "heptahelical receptors" (see, e.g., Schwartz, 1994, Curr. Opin. Biotechnol. 5:434-444)

GPCRs interact with a complex of heterotrimeric guanine nucleotide-binding proteins (G-proteins) and thus regulate a wide variety of intracellular signalling pathways including ion channels. Thus herein a "G protein-coupled cellular response" means a cellular response or signalling pathway that occurs upon ligand binding by a G protein coupled receptor. Such G protein-coupled cellular responses relevant to the present invention are those which modify neuronal excitability and hence neurotransmission. A preferred response is an inhibitory response whereby activation of the receptor with the ligand causes synaptic silencing or inhibition.

One mechanism by which a GPCR may modify neuronal excitability and hence neurotransmission is through inhibition of neurotransmitter release, for example via an effect on presynaptic calcium channels.

Another mechanism by which a GPCR may modify neuronal excitability and hence neurotransmission is through coupling via G-proteins to G protein-coupled inwardly-rectifying potassium channels (GIRKs). The G protein-coupled cellular response here is thus membrane hyperpolarization and neuronal inhibition (11).

Preferred modified receptors of the present invention are GPCRs providing one or both of these cellular responses or activities.

A wide variety of G-protein coupled receptors activate GIRKs, including the $M_2$-muscarinic, $A_1$-adenosine, $α_2$-adrenergic, $D_2$-dopamine, μ- δ-, and κ-opioid, $5$-$HT_{1A}$ serotonin, somatostatin, galanin, m-Glu, $GABA_B$, and sphingosine-1-phosphate receptors (Yamada M, Inanobe A, Kurachi Y (December 1998). "G protein regulation of potassium ion channels". *Pharmacological Reviews* 50 (4): 723-60).

A preferred GPCR which activates GIRKS is the muscarinic acetylcholine receptor $M_4$, also known as the cholinergic receptor. This receptor is a protein that, in humans, is encoded by the CHRM4 gene, and is termed hM4 herein. This is coupled to the $G_i$ alpha subunit (or $G_i/G_O$ or Gi protein). It is believed that hM4Di activation also inhibits neurotransmitter release, most probably mediated by an effect on presynaptic calcium channels. This activity is consistent with evidence for a presynaptic distribution and action of $M_4$ muscarinic receptors, previously reported by Levey et al. J Neurosci 15: 4077-4092, 1995; and Shirey J K, et al. Nat Chem Biol 4: 42-50, 2008.)

Another suitable GPCR may be hM3Dq (also known as hM3D—see 27). This is an excitatory receptor, but in embodiments of the present invention could be expressed in inhibitory neurons in order to achieve an anti-epileptic action.

The modified receptor (RASSL) used herein is modified with respect to its corresponding native G protein-coupled receptor in that the RASSL exhibits binding for a selected natural ligand that is decreased, preferably substantially decreased, more preferably substantially eliminated, relative to binding of the ligand by its corresponding native G protein-coupled receptor.

Therefore RASSL activity is relatively unaffected by natural fluctuations of the selected natural ligand (e.g. acetylcholine). Preferably RASSL binding of the selected natural ligand is decreased by at least 5-fold, preferably 10-fold, more preferably 50-fold, still more preferably 75-fold, and may be decreased 100-fold or more relative to binding by the RASSL's corresponding native G protein-coupled receptor.

RASSLs can also be characterized by the ratio of synthetic ligand binding affinity to binding affinity of a selected natural ligand. Preferably, RASSLs of the invention exhibit a high small molecule ligand binding to selected natural ligand binding ratio, and exhibit small molecule ligand:selected natural ligand binding ratios of at least 0.8, preferably at least 1.0, more preferably at least 5, even more preferably 10, still more preferably 100 or higher.

Preferably, RASSLs exhibit binding ratios that are 2-fold greater, preferably 5-fold greater, more preferably 10-fold greater, even more preferably 50- to 100-fold greater than the small molecule ligand:selected natural ligand binding ratio of a native G protein-coupled receptor.

RASSLs can also be characterized by the ratios of the level of activation by exposure to synthetic ligand to the level of activation by exposure to a selected natural ligand ("activation ratio"). Activation levels can be measured as described below. Preferably, RASSLs of the invention exhibit a high small molecule ligand activation to selected natural ligand activation ratio, and exhibit small molecule ligand:selected natural ligand activation ratios of at least 0.8, preferably at least 1.0, more preferably at least 5, even more preferably 10, still more preferably 100 or higher. Preferably, RASSLs exhibit activation ratios that are 2-fold greater, preferably 5-fold greater, more preferably 10-fold greater, even more preferably 50- to 100fold greater than the small molecule ligand:selected natural ligand activation ratio of a native G protein-coupled receptor.

Channel electrophysiology can be performed as described in (11, supplementary materials and methods). Briefly, receptors are transiently transfected into HEK (tsA201 cells) cells in a 2:1:1 (2 GPCR:1 GIRK1:1 GIRK2) molar ratio using Quantum Prep Cytofectene Transfection Reagent (Bio-Rad). Posttransfection (12-24 h) expression of GIRK channel mediated $K^+$ currents are verified by 50-ms voltage ramps from −100 to +50 mV from 0 mV by their inward rectifying properties. The following extracellular and intracellular recording solution are used; extracellular (20 mM NaCl/120 mM KCl/2 mM $CaCl_2$/1 mM $MgCl_2$/10 mM Hepes-NaOH, pH 7.3 with KOH), intracellular (100 mM K-aspartate/40 mM KCl/5 mM MgATP/10 mM Hepes-KOH/5 mM NaCl/2 mM EGTA/2 mM $MgCl_2$/10 mM GTP, pH 7.3 with KOH). Once currents are identified, HEK cells were voltage-clamped at −60 mV for 15-60 sec and either 10 mM CCh or CNO is applied directly onto the cells for 2 sec using a fast flow perfusion system (ALA Scientific Instruments, Westbury, N.Y.).

As an alternative one could utilise methods based on those of Tomlinson S E, Rajakulendran S, Tan S V, et al. J Neurol Neurosurg Psychiatry 2013; 84: 1107-1112. cDNA encoding the GPCR, GIRK subunits and green fluorescent protein (GFP) contained within the plasmid pMT2LF are transiently transfected into human embryonal kidney (HEK) cells in a 2:1:1:1 (2 GPCR:1 GIRK1:1 GIRK2:1 GFP) molar ratio using lipofectamine2000 (Invitrogen). Recordings are made 36-72 h after transfection. Whole-cell patch clamp recordings are performed at room temperature. The external solution contains (in mM): $NaCl_2$ 135; KCl 4; $MgCl_2$ 1; $CaCl_2$ 2; HEPES 10. The pipette solution contains (in mM): NaCl 135; KCl 2.5; EGTA 2; HEPES 10. Pipette resistance is 2-4MΩ when filled with intracellular solution. Cells expressing GFP are held at −80 mV, and series resistance is not compensated. Cells with series resistance above 10 MΩ are discarded. A −P/4 protocol is used to subtract leak currents. Currents are recorded using an Axopatch 200B or Axoclamp 700B amplifier (Molecular Devices). Data are acquired and analysed using LabView software (National Instruments).

For monitoring membrane potential of cultured hippocampal neurons, Sprague-Dawley rat pups (Zivic Miller Inc., Pittsburgh, Pa.) are killed at postnatal day 1 and hippocampal neurons are dissociated and cultured on coverslips. Neurons (10-14 day old) are infected with Sindbis virus and 12-24 h postinfection were used for recordings. Alternatively, and preferably, lentivirus can be used. Briefly, lentivirus expressing the GPCR and GFP is added one day after plating neurons, and recordings are obtained after 14 days in vitro (Heeroma J H, Henneberger C, Rajakulendran S, Hanna M G, Schorge S, Kullmann D M, Disease Models & Mechanisms 2, 612-619, 2009). Hippocampal neurons are recorded in extracellular buffer (172 mM NaCl/2.4 mM KCl/10 mM Hepes/10 mM glucose/4 mM $CaCl_2$/4 mM $MgCl_2$, pH 7.3) and intracellular buffer (145 mM $K^+$ gluconate/15 mM Hepes/1 mM $K^+$-EGTA/4 mM Na-ATP/0.4 mM Na-GTP, pH 7.3). Changes in the membrane potential of hippocampal neurons are performed in the current clamp mode and either CCh or CNO were directly applied onto the cell as described above. For recording of the action potential firing 10 μM bicuculline (Sigma) is added to the extracellular recording solution to block the inhibitory input into hippocampal neurons. Patch-clamp recordings are performed with a Multiclamp 700B (Molecular Devices) amplifier. Currents were digitized at 10 kHz and filtered with the internal 10-kHz three-pole Bessel filter (filter1) in series with a 2.9-kHz 4-pole Bessel filter (filter 2).

To characterise the effect of GPCRs on synaptic transmission 1 μl of adeno-associated virus serotype 5 (AAV5) expressing the GPCR and the fluorescent reporter protein mCitrine is injected into the CA3 subfield of the dorsal hippocampus of male Sprague-Dawley rats (4 weeks old) at 3.6 mm lateral (right), 2.8 mm posterior and 2.9 mm ventral from bregma at 100 nl/min (Akam T, Oren I, Mantoan L, Ferenczi E, Kullmann D M. Nat Neurosci 2012 May; 15(5):763-8). 4-6 weeks later, animals are transcardially perfused with room temperature solution containing (in mM): N-Methyl-D-glucamine, 92; KCl, 2.5; $NaH_2PO_4$, 1.25; Thiaurea, 2; Ascorbic acid, 5; Na-Pyruvate, 3; $MgCl_2$, 10; D-Glucose, 25; $NaHCO_3$, 30; $CaCl_2$, 0.5; Sucrose, 1, and horizontal hippocampal slices prepared. The extracellular perfusion solution contains (in mM): NaCl, 119; KCl, 2.5; $CaCl_2$, 0.5; $MgSO_4$, 1.3; $MgCl$, 2; $NaH_2PO_4$, 1.25; $NaHCO_3$, 25; Glucose, 10. A field excitatory postsynaptic potential (fEPSP) is evoked every 30 seconds by extracellular stimulation (20-320 μA 100 μs) in stratum radiatum of CA1, before, during and after bath perfusion of CNO (10 μM).

A preferred Gi-coupled human muscarinic receptor is "hM4Di", which has been made sensitive to the orally bioavailable and normally inert metabolite of clozapine, clozapine-N-oxide (CNO) (11, 12). This modified GPCR includes the following mutations: Y113C/A203G. Preferably the modified receptor is encoded by SEQ ID NO: 1.

Importantly, hM4Di is relatively insensitive to acetylcholine, the endogenous agonist of the parent receptor.

The modified receptor hM4Di was originally described in Reference 11 (B. N. Armbruster, X. Li, M. H. Pausch, S. Herlitze, B. L. Roth, "Evolving the lock to fit the key to create a family of G protein-coupled receptors potently activated by an inert ligand", *Proc. Natl. Acad. Sci. USA*. 104, 5163-5168 (2007)). Those authors describe a general, validated and unbiased approach for generating GPCRs with defined ligand specificities, which was utilised to create a family of muscarinic ACh receptor (mAChR) DREADDs. The content of that publication, in respect of its description of the preparation and characteristics of these DREADDs, is specifically incorporated herein by reference. Armbruster et al. (11) also teaches that human muscarinic acetylcholine receptors mutated to DREADDs as described are readily activated by clozapine-related ligands, such as clozapine, CNO and olanzapine.

The preparation of a human M4 DREADD is also described in Nawaratne, V., Leach, K., Suratman, N., Loiacono, R. E., Felder, C. C., Armbruster, B. N., & Christopoulos, A. (2008). "New insights into the function of M4 muscarinic acetylcholine receptors gained using a novel allosteric modulator and a DREADD (designer receptor exclusively activated by a designer drug)". *Molecular pharmacology*, 74(4), 1119-1131.

A plasmid encoding hM4Di is available commercially as plasmid 45548: pcDNA5/FRT-HA-hM4D(Gi) from Addgene, Cambridge, Mass. 02139 (http://www.addgene.org/45548/) and is described in the sequence annex and Figures hereinafter.

A plasmid encoding hM3Dq is also available commercially from Addgene (https://www.addgene.org/44361/) as well as being described in reference (19). This receptor is sensitive to perlapine (27)

Vectors & Administration Thereof

Any of a variety of vectors can be used in accordance with the invention to produce RASSL-expressing cells.

A vector for use in the therapies of the present invention will be suitable for in vivo gene therapy protocols. The vector may be a stable integrating vector or a stable nonintegrating vector. A preferred vector is viral vector, such as a lentiviral or AAV (Adeno-associated virus) vector.

The use of both these types of viral vector is well known in the art for gene therapy. By way of example only, WO2008011381 describes the use of these and other vectors for expressing receptors in a subject. The content of that application, in respect of its description of the preparation and characteristics of AAV and lentiviral vectors is specifically incorporated herein by reference.

Briefly, as described in WO2008011381, AAV is a defective parvovirus and is a preferred vector because it can infect many cell types and is nonpathogenic to humans. AAV type vectors can transport about 4 to 5 kb and wild type AAV is known to stably insert into chromosome 19. Vectors which contain this site specific integration property are preferred.

An especially preferred embodiment of this type of vector is the P4.1 C vector produced by Avigen, San Francisco, Calif. In another type of AAV vector, the AAV contains a pair of inverted terminal repeats (ITRs) which flank at least one cassette containing a promoter which directs cell-specific expression operably linked to a heterologous gene (here: a RASSL). Further information can be found in U.S. Pat. No. 6,261,834.

Lentiviral vectors are a special type of retroviral vector which are typically characterized by having a long incubation period for infection. Furthermore, lentiviral vectors can infect non-dividing cells. Lentiviral vectors are based on the nucleic acid backbone of a virus from the lentiviral family of viruses. Typically, a lentiviral vector contains the 5' and 3' LTR regions of a lentivirus, such as SIV and HIV. Lentiviral vectors also typically contain the Rev Responsive Element (RRE) of a lentivirus, such as SIV and HIV. Examples of lentiviral vectors include those of Dull, T. et al., "A Third-generation lentivirus vector with a conditional packaging system" J. Virol 72(11):8463-71 (1998);

The vectors described herein can be delivered locally to the target cells in a variety of access methods known in the art—see e.g. "Stereotactic and Functional Neurosurgery" Editors: Nikkhah & Pinsker; Acta Neurochirurgica Supplement Volume 117, 2013. In particular delivery can be via direct injection into the brain using known methodologies, such as burr-hole craniotomy and stereotactic injection. The injection will be targeted to a seizure focus where that has been defined (e.g. in focal epilepsy) or more generally into areas of the brain suspected of overactivity in other seizure diseases.

Vectors may be used to effect permanent transformation, or may be only be transiently expressed in the brain.

Generally speaking, those skilled in the art are well able to construct vectors and design protocols for recombinant gene expression. Suitable vectors can be chosen or constructed, containing, in addition to the elements of the invention described above, appropriate regulatory sequences, including promoter sequences, terminator fragments, polyadenylation sequences, marker genes and other sequences as appropriate. For further details see, for example, Molecular Cloning: a Laboratory Manual: 2nd edition, Sambrook et al, 1989, Cold Spring Harbor Laboratory Press or Current Protocols in Molecular Biology, Second Edition, Ausubel et al. eds., John Wley & Sons, (1995, and periodic supplements).

Preferably, the DNA construct contains a promoter to facilitate expression of the RASSL-encoding DNA within the target cell. Specificity can be achieved by regional and cell-type specific expression of the receptor exclusively e.g. using a tissue or region specific promoter.

An example is the Camk2a (alpha CaM kinase II gene) promoter, which drives expression in relatively specifically in the forebrain—see e.g. Sakurada et al (2005) "Neuronal cell type-specific promoter of the alpha CaM kinase II gene is activated by Zic2, a Zic family zinc finger protein." Neurosci Res. 2005 November; 53(3):323-30. Epub 2005 Sep. 12.

Other neuronal cell type-specific promoters include the NSE promoter (Liu H. et al., Journal of Neuroscience. 23(18):7143-54, 2003); tyrosine hydroxylase promoter (Kessler M A. et al., Brain Research. Molecular Brain Research. 112(I-2):8-23, 2003); myelin basic protein promoter (Kessler M A. et al Biochemical & Biophysical Research Communications. 288(4):809-18, 2001); glial fibrillary acidic protein promoter (Nolte C. et al., GLIA. 33(I):72-86, 2001); neurofilaments gene (heavy, medium, light) promoters (Yaworsky P J. et al., Journal of Biological Chemistry. 272(40):25112-20, 1997) (All of which are herein incorporated by reference at least for the sequence of the promoters and related sequences.) The NSE promoter is disclosed in Peel A L. et al., Gene Therapy. 4(1): 16-24, 1997) (SEQ ID NO:69) (pTR-NT3myc; Powell Gene Therapy Center, University of Florida, Gainesville Fla.). A further suitable promoter is the Synapsin1 promoter (see Kügler et al "Human synapsin 1 gene promoter confers highly neuron-specific long-term transgene expression from an adenoviral vector in the adult rat brain depending on the transduced area." Gene Ther. 2003 February; 10(4):337-47).

Agonists & Administration Thereof

In the present invention, the modified receptor is activated by the presence of an exogenous agonist. The exogenous agonist (or ligand, or small molecule, the terms are used interchangeably herein) is one which can be delivered orally or parenterally (e.g. systemically administered) and penetrate the blood-brain barrier. The ligand is exogenous in that it is generally absent from the brain, or present in sufficiently low basal concentrations that it does not activate the modified receptor.

Preferably the half-life in brain of the ligand is less than 120, 60, or 30 minutes. This has the advantage that any side effect on normal brain function caused by interaction of the ligand and receptor is minimised.

Preferably the ligand is synthetic i.e. not naturally occurring.

Preferred ligand(s) are those possessing minimal or no biologic activity other than RASSL activation.

Any small molecule, preferably a synthetic small molecule, that can bind within the transmembrane domains of a RASSL and facilitate RASSL-mediated activation of a desired family of G proteins is suitable for use in the method of targeted activation method of the invention. In contrast to the natural peptide ligands of G protein-coupled receptors which typically have molecular weights of 2000-6000 Da, small molecule ligands of G protein-coupled receptors will generally have molecular weights of 100-1000 Da.

Synthetic small molecules useful in the present invention include synthetic small molecules generated by either a natural (e.g., isolated from a recombinant cell line) or chemical means (e.g., using organic or inorganic chemical processes).

The ligand will generally have a molecular weight and net ionic charge that permits it to cross the blood-brain barrier following oral or parenteral (e.g., intravenous) administration.

Typically molecules that cross the blood brain barrier are less charged than peptide molecules. Synthetic drugs can be made that do, or do not cross the blood-brain barrier depending on the number of charged groups on the molecule (see, e.g., Freidinger, 1993, Prog. Drug Res. 40:33-98). Smaller molecules, e.g., less than 4000 Da, are also more likely to cross the blood-brain barrier.

Several synthetic small molecules that bind and activate native G protein-coupled receptors are known in the art and are useful in the present invention. Additional synthetic small molecules suitable for use in the present invention can be identified by screening candidate compounds for binding to native G protein-coupled receptors or to RASSLs. For example by assessing channel electrophysiology and measuring membrane potentials of cultured neurons, as described above. In particular, a cell line expressing (or transfected with) a RASSL and associated potassium channels of interest, and is exposed to varying concentrations of a compound to be tested for RASSL binding. RASSL binding is detected by induction of membrane hyperpolarization and neuronal inhibition (11) upon exposure to the test compound, but not in the presence of a control compound that does not bind the RASSL and/or does not induce cellular activation.

In a preferred embodiment the ligand is clozapine-N-oxide (CNO), which is a metabolite of clozapine. This can be delivered by a variety of routes, as described herein, including buccally or intranasally.

Another preferred ligand is perlapine, which binds to hM3Dq (27). Since the binding sites of hM3Dq and hM4Di are highly similar, it can likewise be expected to bind hM4Di.

Disorders

In preferred embodiments, the seizure disorder is epilepsy, for example idiopathic, symptomatic and cryptogenic epilepsy. The methods described herein may be used to quench or blocking epileptogenic activity. The methods may be used for raising the seizure threshold in brain or neural tissue of a patient in need thereof, or reducing epileptic bursting in brain cells of the patient.

The combined chemical-genetic (also known as chemogenetic) methods of the present invention are particularly suitable for the treatment of human focal epilepsy, for the suppression of seizures in a region- and time-specific manner.

The patient may be one who has been diagnosed as having well defined focal epilepsy affecting a single area of the neocortex of the brain. Focal epilepsy can arise, for example, from developmental abnormalities or following strokes, tumours, penetrating brain injuries or infections.

However the invention may also be used to treat multiple epileptic foci simultaneously by injection directly into the multiple identified loci.

The patient may be one who has been diagnosed as having drug-resistant or medically-refractory epilepsy, by which is meant that epileptic seizures continue despite adequate administration of antiepileptic drugs.

The patient may be one who is under an existing treatment with anti-epileptic drugs, wherein the method has the purpose of permitting the existing treatment to be discontinued or the drug regime to be reduced.

The patient may be one who has been diagnosed as having epilepsia partialis continua.

The treatments of the present invention have particular utility where a permanent reduction in neuronal excitability (as could be achieved with potassium channel overexpression, for instance) is undesirable, for example because it represents too great a risk to normal brain function. Even if the epileptogenic zone is in the cortical regions responsible for language or motor function, there would be no effect on these functions except when the ligand was administered. Patients with intractable focal epilepsy are likely to consider this an acceptable side effect.

Although the invention has particular utility for seizure disorders characterized by focal onset, such as temporal lobe epilepsy and focal neocortical epilepsy, it may also be applied to more generalised forms epilepsy, particularly as a second-line indication. In these cases the target for delivery will be chosen as appropriate to the condition e.g. delivery may be bilaterally to the thalamus. Thus other disorders to which the invention may be applied include infantile spasms, myoclonic and "minor motor" seizures, as well as tonic-clonic seizures and partial complex seizures.

Furthermore, in principle, the invention could be used prophylactically by causing continued alteration of neuronal excitability for a fixed period with the purpose of 'resetting' epileptogenic circuits in some circumstances, bringing about a persistent reduction in seizures that outlasts the administration of the ligand.

Administration & Dosage

Most epilepsy patients have a stereotyped pattern of activity spread resulting from an epileptogenic focus. The invention may thus be applied prophylactically (e.g. up to 30 minutes before) to suppress the abnormal activity before it spreads, or to truncate it early in its course. Furthermore because seizures often occur in clusters, patients can if desired take the ligand when a cluster started.

The ligand could be administered by a carer.

The ligand could be delivered automatically by a device that was coupled to an automated seizure detection mechanism. For example on-demand administration, could be used with subcutaneous pumps (as used to deliver insulin (23; 25)). Recent evidence that seizures can be predicted by automated EEG analysis (22) provides for the option of using a closed loop device to administer the ligand.

The term "treatment," as used herein in the context of treating a condition, pertains generally to treatment and therapy of a human, in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The ligand can be delivered in a therapeutically-effective amount.

The term "therapeutically-effective amount" as used herein, pertains to that amount of the receptor or ligand which is effective for producing some desired therapeutic effect, commensurate with a reasonable benefit/risk ratio, when administered in accordance with a desired treatment regimen.

Similarly, the term "prophylactically effective amount," as used herein pertains to that amount of the receptor or ligand which is effective for producing some desired prophylactic effect, commensurate with a reasonable benefit/risk ratio, when administered in accordance with a desired treatment regimen.

"Prophylaxis" in the context of the present specification should not be understood to circumscribe complete success i.e. complete protection or complete prevention. Rather prophylaxis in the present context refers to a measure which is administered in advance of detection of a symptomatic condition with the aim of preserving health by helping to delay, mitigate or avoid that particular condition.

While it is possible for the ligand to be used (e.g., administered) alone, it is often preferable to present it as a composition or formulation e.g. with a pharmaceutically acceptable carrier or diluent.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

In some embodiments, the composition is a pharmaceutical composition (e.g., formulation, preparation, medicament) comprising, or consisting essentially of, or consisting of as a sole active ingredient, a ligand as described herein, and a pharmaceutically acceptable carrier, diluent, or excipient.

As described in WO2008096268, in gene therapy embodiments employing viral delivery of the modified receptor, the unit dose may be calculated in terms of the dose of viral particles being administered. Viral doses include a particular number of virus particles or plaque forming units (pfu). For embodiments involving adenovirus, particular unit doses include $10^3$, $10^4$, $10^5$, $10^6$, $10^7$, $10^8$, $10^9$, $10^{10}$, $10^{11}$, $10^{12}$, $10^{13}$ or $10^{14}$ pfu. Particle doses may be somewhat higher (10 to 100 fold) due to the presence of infection-defective particles.

In some embodiments the methods or treatments of the present invention may be combined with other therapies, whether symptomatic or disease modifying.

The term "treatment" includes combination treatments and therapies, in which two or more treatments or therapies are combined, for example, sequentially or simultaneously.

For example it may be beneficial to combine treatment with a compound as described herein with one or more other (e.g., 1, 2, 3, 4) agents or therapies.

Appropriate examples of co-therapeutics will be known to those skilled in the art on the basis of the disclosure herein. Typically the co-therapeutic may be any known in the art which it is believed may give therapeutic effect in treating the diseases described herein, subject to the diagnosis of the individual being treated. For example epilepsy can sometimes be ameliorated by directly treating the underlying etiology, but anticonvulsant drugs, such as phenytoin, gabapentin, lamotrigine, levetiracetam, carbamazepine and clobazam, and topiramate, and others, which suppress the abnormal electrical discharges and seizures, are the mainstay of conventional treatment (Rho & Sankar, 1999, Epilepsia 40: 1471-1483).

The particular combination would be at the discretion of the physician who would also select dosages using his/her common general knowledge and dosing regimens known to a skilled practitioner.

The agents (i.e. the modified receptor and ligand, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g., 1, 2, 3, 4 or more hours apart, or even longer periods apart where required), the precise dosage regimen being commensurate with the properties of the therapeutic agent(s).

Selected Definitions

"Receptor-ligand binding," "ligand binding," and "binding" are used interchangeably herein to mean physical interaction between a receptor (e.g., a G protein-coupled receptor) and a ligand (e.g., a natural ligand, (e.g., peptide ligand) or synthetic ligand (e.g., synthetic small molecule ligand)). Ligand binding can be measured by a variety of methods known in the art (e.g., detection of association with a radioactively labeled ligand).

"Signaling" means the generation of a biochemical or physiological response as a result of ligand binding (e.g., as a result of synthetic ligand binding to a G protein-coupled receptor).

"Receptor activation," "RASSL activation," and "G protein-coupled receptor activation" are used interchangeably herein to mean binding of a ligand (e.g., a natural or synthetic ligand) to a receptor in a manner that elicits G protein-mediated signaling, and a physiological or biochemical response associated with G protein-mediated signaling. Activation can be measured by measuring a biological signal associated with G protein-related signals (e.g. using electrophysiology)

"Targeted cellular activation" and "target cell activation" are used interchangeably herein to mean RASSL mediated activation of a specific G protein-mediated physiological response in a target cell, where RASSL-mediated activation occurs by binding of a synthetic small molecule to the RASSL. As used herein, cellular activation includes inhibitory responses such as synaptic silencing or inhibition.

"Natural ligand" and "naturally occurring ligand" and "endogenous ligand" of of a native G protein-coupled receptor are used interchangeably herein to mean a biomolecule endogenous to a mammalian host, which biomolecule binds to a native G protein-coupled receptor to elicit a G protein-coupled cellular response. An example is acetyl-choline.

"Synthetic small molecule, "synthetic small molecule ligand," "synthetic ligand", and "synthetic agonist" and the like are used interchangeably herein to mean any compound made exogenously by natural or chemical means that can bind within the transmembrane domains of a G protein-coupled receptor or modified G protein-coupled receptor (i.e., RASSL) and facilitate activation of the receptor and concomitant activation of a desired family of G proteins.

"Transformation" means a transient or permanent genetic change induced in a cell following incorporation of new DNA (i.e., DNA exogenous to the cell). Where the cell is a mammalian cell, a permanent genetic change is generally achieved by introduction of the DNA into the genome of the cell.

"Promoter" means a minimal DNA sequence sufficient to direct transcription of a DNA sequence to which it is operably linked. "Promoter" is also meant to encompass those promoter elements sufficient for promoter-dependent gene expression controllable for cell-type specific, tissue specific or inducible by external signals or agents; such elements may be located in the 5' or 3' regions of the native gene.

Variants of Nucleic Acids

It will be understood by those skilled in the art that functional variants derived from the sequences discussed herein (see SEQ ID 1 in the sequence annex) above may likewise be employed in the present invention.

Preferred functional derivatives of the agent include proteins that may comprise mutations (relative to the wild type) that nevertheless do not alter the activity of the agent. In accordance with the present invention, preferred further changes in the agent are commonly known as "conservative" or "safe" substitutions. Conservative amino acid substitutions are those with amino acids having sufficiently similar chemical properties, in order to preserve the structure and the biological function of the agent. It is clear that insertions and deletions of amino acids may also be made in the above defined sequences without altering their function, particularly if the insertions or deletions only involve a few amino acids, e.g. under ten and preferably under five, and do not remove or displace amino acids which are critical to the functional confirmation of the agent. The literature provide many models on which the selection of conservative amino acids substitutions can be performed on the basis of statistical and physico-chemical studies on the sequence and/or the structure of a natural protein.

It will be appreciated by the skilled technician that functional derivatives of the amino acid, and nucleic acid sequences, disclosed herein, may have a sequence which has at least 30%, preferably 40%, more preferably 50%, and even more preferably, 60% sequence identity with the amino acid/polypeptide/nucleic acid sequences of any of the sequences referred to herein. An amino acid/polypeptide/nucleic acid sequence with a greater identity than preferably 65%, more preferably 75%, even more preferably 85%, and even more preferably 90% to any of the sequences referred to is also envisaged. Preferably, the amino acid/polypeptide/nucleic acid sequence has 92% identity, even more preferably 95% identity, even more preferably 97% identity, even more preferably 98% identity and, most preferably, 99% identity with any of the referred to sequences.

In each case the modified receptor will retain the properties in the terms defined above e.g. targeted cellular activation in the presence of the agonist, but not the natural ligand.

Calculation of percentage identities between different amino acid/polypeptide/nucleic acid sequences may be carried out as follows. A multiple alignment is first generated by the ClustalX program (pair wise parameters: gap opening 10.0, gap extension 0.1, protein matrix Gonnet 250, DNA matrix IUB; multiple parameters: gap opening 10.0, gap extension 0.2, delay divergent sequences 30%, DNA transition weight 0.5, negative matrix off, protein matrix Gonnet series, DNA weight IUB; Protein gap parameters, residue-specific penalties on, hydrophilic penalties on, hydrophilic residues GPSNDQERK, gap separation distance 4, end gap separation off). The percentage identity is then calculated from the multiple alignment as (N/T)*100, where N is the number of positions at which the two sequences share an identical residue, and T is the total number of positions compared. Alternatively, percentage identity can be calculated as (N/S)*100 where S is the length of the shorter sequence being compared. The amino acid/polypeptide/nucleic acid sequences may be synthesised de novo, or may be native amino acid/polypeptide/nucleic acid sequence, or a derivative thereof.

Due to the degeneracy of the genetic code, it is clear that any nucleic acid sequence could be varied or changed without substantially affecting the sequence of the agent protein encoded thereby, to provide a functional variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequence which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid.

Any sub-titles herein are included for convenience only, and are not to be construed as limiting the disclosure in any way.

The invention will now be further described with reference to the following non-limiting Figures and Examples. Other embodiments of the invention will occur to those skilled in the art in the light of these.

The disclosure of all references cited herein, inasmuch as it may be used by those skilled in the art to carry out the invention, is hereby specifically incorporated herein by cross-reference.

FIGURES (FROM REF. 26)

FIG. 1. Chemical-genetic silencing of pilocarpine-induced seizures. (a) Morlet-wavelet EEG spectra from a rat administered intracortical pilocarpine (time 0), with either intraperitoneal vehicle (top) or CNO (bottom). (b) EEG segment from (a, top), showing simple spikes (SS), complex spikes (CS) and runs of intermediate frequency (IF) activity (expanded below). (c) Behavioural seizures correlated with EEG. SS activity was associated with no motor seizures (severity score 0) or twitching of limb, head or body (score 1), while IF was associated with repetitive head or body shaking (score 2) or rearing, retrograde locomotion and generalized convulsions (3). Six hundred consecutive 4-s-intervals per rat were assessed in three rats (numbered 1-3). (d) Detection of Intermediate Frequency (IF)-activity by Fourier transformation: Fourier transform (right) of EEG segments in one rat showing either SS (black) or IF (red) activity (two 5-s periods shown to the left) induced by pilocarpine. The IF Fourier transform shows a peak around 7 Hz (and a harmonic at 14 Hz). (e) Temporal evolution of spike frequency (left), 4-14 Hz power (middle), and number of IF runs (right), in vehicle (red) and CNO (blue) trials (consecutive 10-min-intervals before (−10-0 min) and after pilocarpine and vehicle/CNO injection). N=6 rats (10 pairs of trials, averaged within rat where repeated, data are shown as mean±s.e.m.). (f) Same data as in e, but plotted as cumulative electrographic seizure metrics (frequency, power, number of IF events), comparing vehicle versus CNO for each animal (indicated by colour). Symbols indicate consecutive cumulative metrics at 10-min-intervals. The 45-degree line (grey) indicates equivalence of CNO and vehicle.

Figure 2:
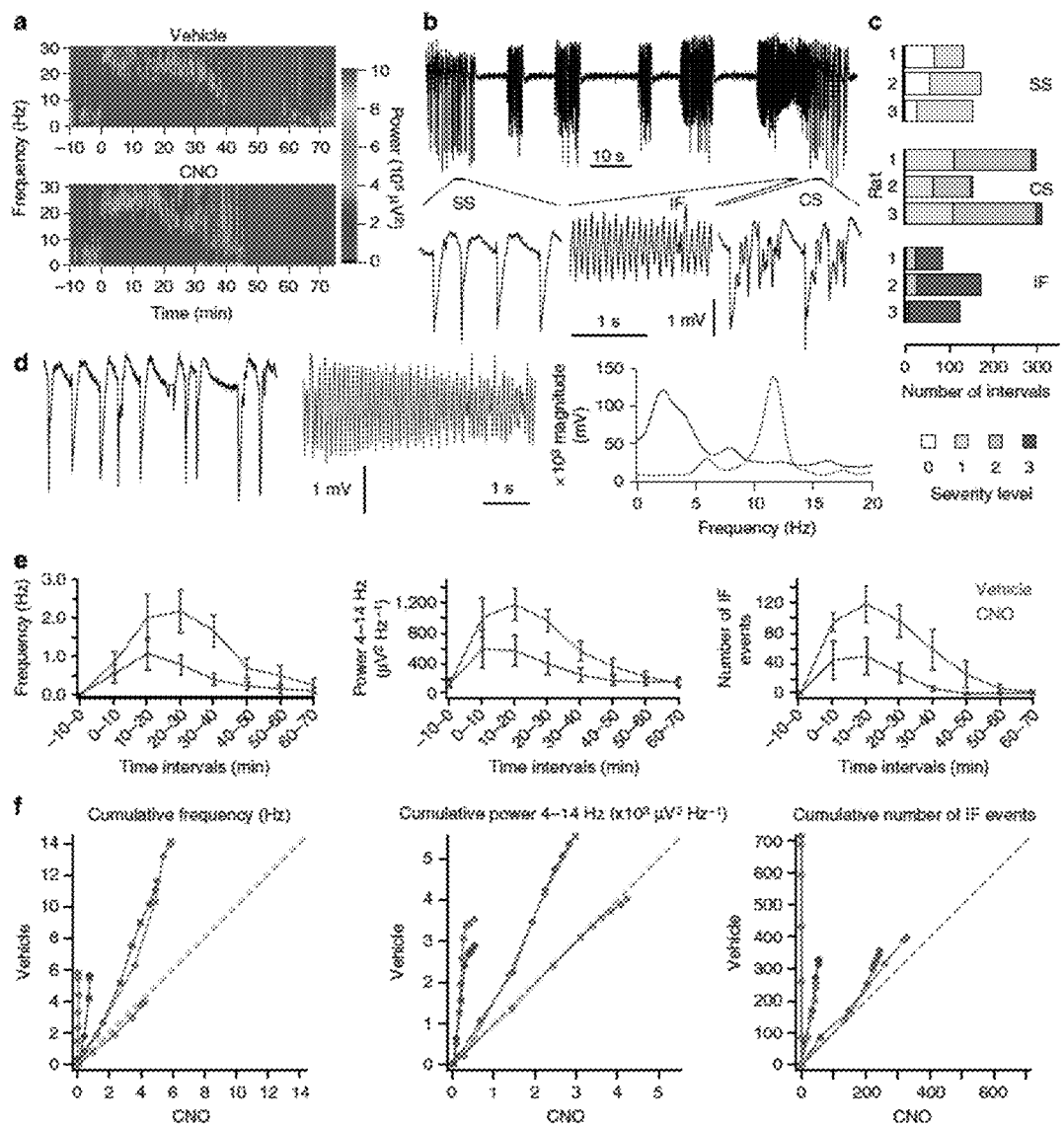

FIG. 2. Chemical-genetic silencing of picrotoxin-induced seizures. (a) Morlet-wavelet power spectra of EEG in an animal injected with picrotoxin at time 0 (1 mm below pia, 10 mM, 300 nl), together with intraperitoneal vehicle (top) or 1 mg ml-1 CNO in vehicle (bottom) on consecutive days. (b) EEG activity. Bottom, expanded sections from times indicated (2-s-duration) showing SS, CS and IF activity. (c) Motor seizures were more severe in association with IF activity than with SS activity, and intermediate with CS activity (severity scale as in FIG. 2c). Six hundred consecutive 4-s-intervals per rat were assessed in three rats (numbered 1-3). (d) Fourier transform (right) of 5-s-traces displayed (left, middle) containing SS (black) and IF (4-14 Hz, peak around 11.5 Hz; red) activity induced by picrotoxin. (e) Temporal evolution of spike frequency (left), 4-14 Hz power (middle), and number of IF runs (right), in vehicle (red) and CNO (blue) trials (consecutive 10-min-intervals before (−10-0 min) and after picrotoxin and vehicle/CNO injection). N=5 rats (12 pairs of trials, averaged within rat where repeated, mean±s.e.m.). (f) Same data as in e, but plotted as cumulative electrographic seizure metrics for each animal as in FIG. 2e.

Figure 3:
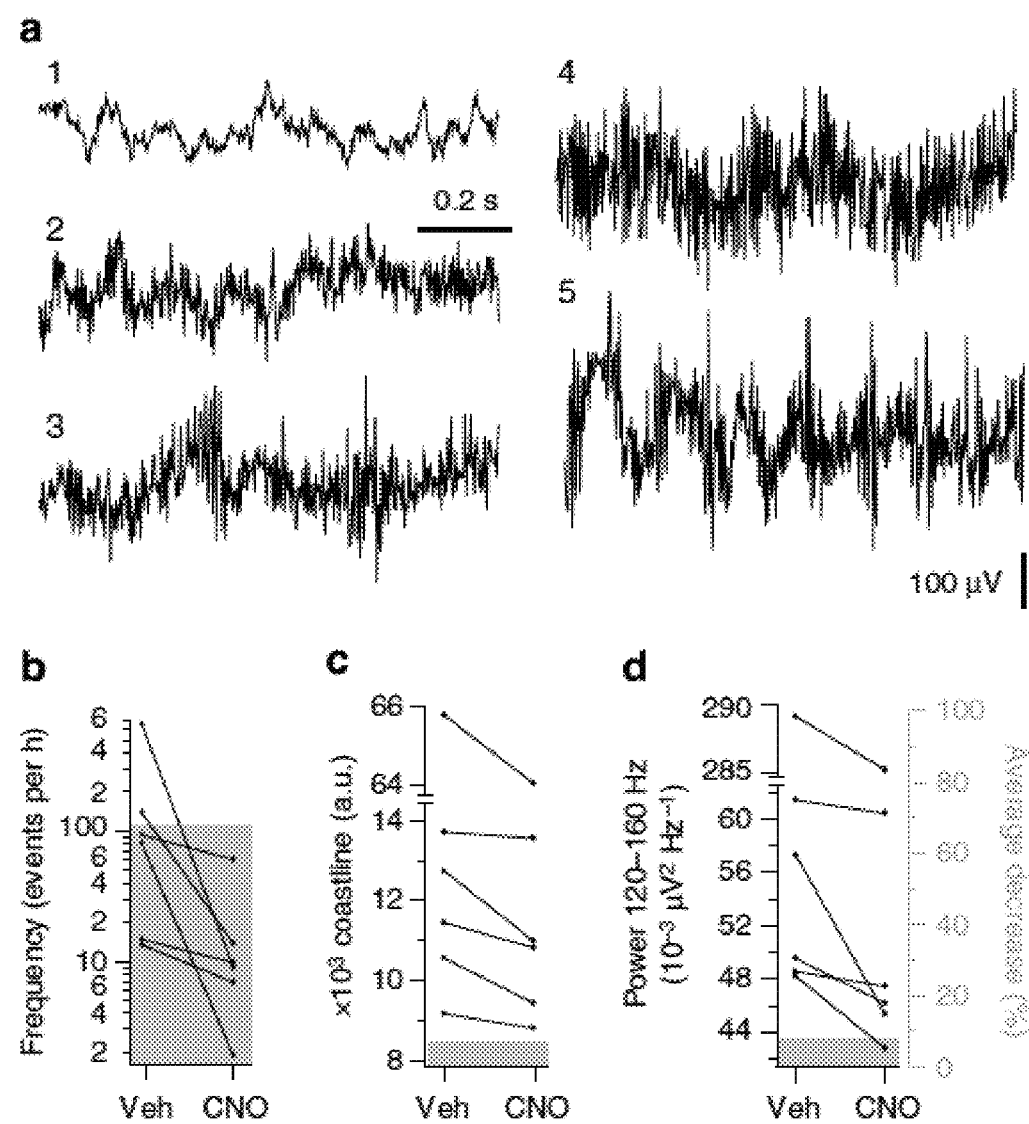

FIG. 3. Chemical-genetic silencing of focal neocortical epilepsy induced by tetanus toxin. (a) Sample EEG traces from a tetanus toxin injected animal, showing background activity (1) and four types of epileptiform activity: 'long events of low amplitude' (2), 'short events of high amplitude' (3), 'long event of high amplitude' (4), and 'high amplitude plus intermittent spikes' (5). (b-d) Pair-wise comparison of the frequency of epileptiform events (b), coastline (c) and high-frequency power (d) between vehicle and CNO trials. N=6 rats; 15 pairs of trials, averaged within animal where repeated. Orange bars indicate the decrease (%, right axis), where significant (Wlcoxon test; P<0.05).

Figure 4:
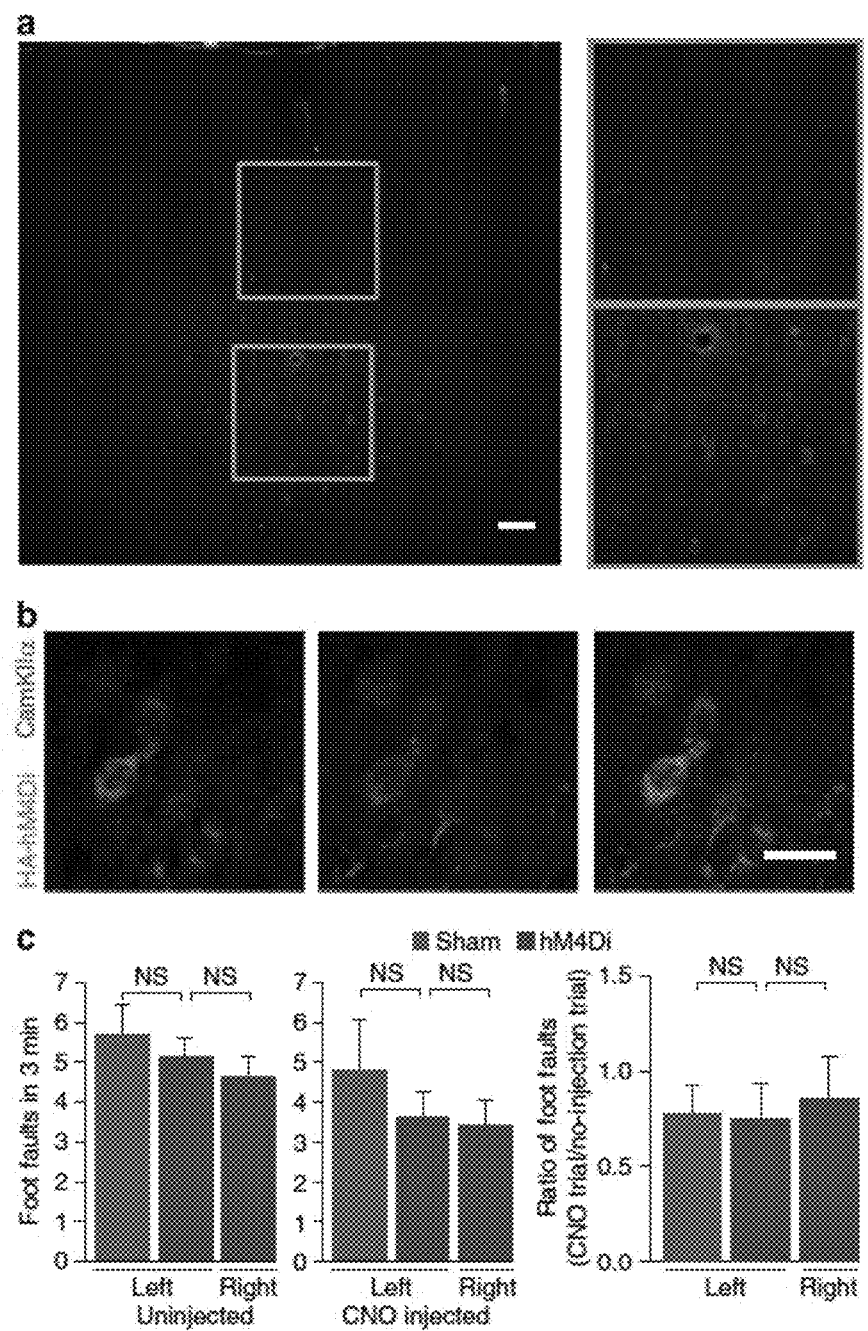

FIG. 4. Expression and tolerability of HA-hM4D$_i$-mCitrine. (a) Expression of HA-hM4Di-mCitrine in deeper layers of right primary motor cortex (M1), visualized with anti-HA antibody. Scale, 100 µm. (b) Colocalization of CamKIIα-HA-hM4Di-mCitrine, visualized with anti-HA (left) and anti-CamKIIα (middle), and both (right) antibodies. Scale, 20 µm. (c) Motor coordination with (right) and without (left) intraperitoneal CNO in rats receiving sham injection (left hand bar) or HA-hM4Di-mCitrine in right M1 (middle and right hand bars). Foot faults for the left forelimb (contralateral to HA-hM4Di-mCitrine) were compared with the right (ipsilateral) forelimb (paired t-test) and with foot faults of the left forelimb of sham-injected animals (unpaired t-test; mean±s.e.m., n=5 sham-operated and 7 hM4-injected rats). NS: P>0.05.

Figure 5:
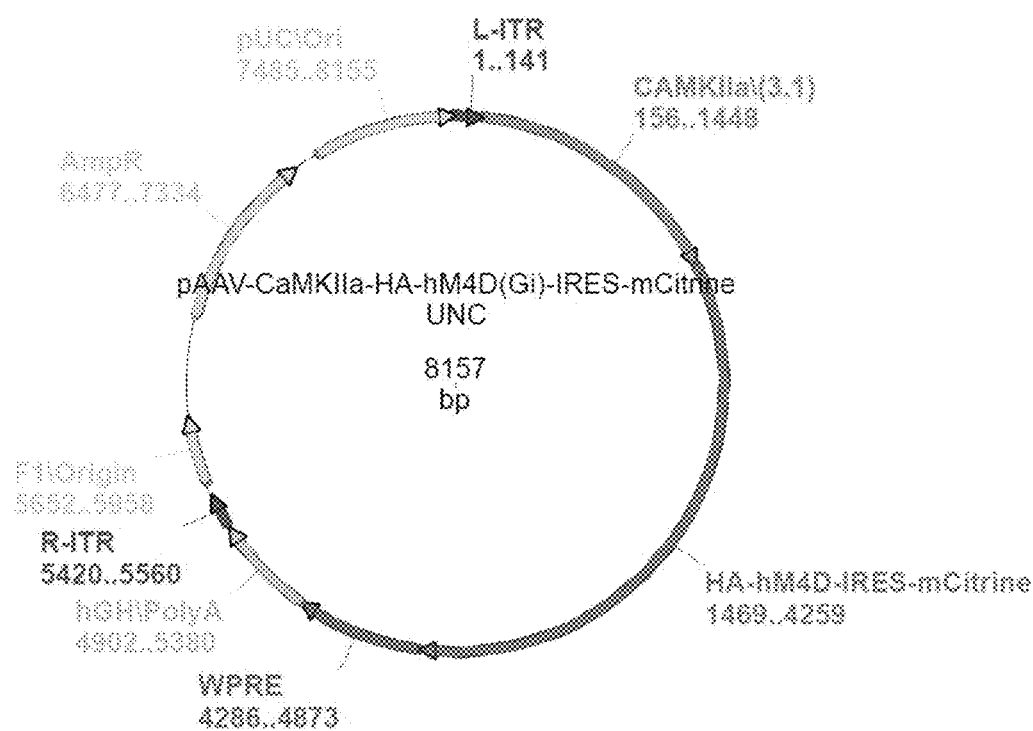

FIG. 5. Map of viral (AAV) vector in (plasmid: 5421-8155 bp) used to deliver hM4Di, as explained in the Examples below.

EXAMPLES

Example 1—Demonstration of Chemical-Genetic Therapy in a Model of Epilepsy

Introduction and Overview

We have demonstrated a combined chemical-genetic approach to achieve localized suppression of neuronal excitability in a seizure focus, using viral expression of a DREADD (Designer Receptors Exclusively Activated by Designer Drugs). Neurons transduced with a DREADD are in principle unaffected in the absence of the selective ligand, and untransduced neurons are only affected when the ligand is present, thereby avoiding permanent alteration of their properties (10).

We chose the engineered Gi-coupled human muscarinic receptor hM4Di, which has been made sensitive to the orally bioavailable and normally inert metabolite of clozapine, clozapine-N-oxide (CNO) (11, 12). Importantly, hM4Di is relatively insensitive to acetylcholine, the endogenous agonist of the parent receptor. hM4Di activation leads to the opening of G-protein gated inwardly rectifying potassium channels, resulting in membrane hyperpolarization and neuronal inhibition (11).

Systemic administration of CNO suppressed focal seizures evoked by two different chemoconvulsants, pilocarpine and picrotoxin. CNO also had a robust anti-seizure effect in a chronic model of focal neocortical epilepsy. Chemical-genetic seizure attenuation provides a novel approach to treat intractable focal epilepsy whilst minimizing disruption of normal circuit function in untransduced brain regions or in the absence of the specific ligand.

Materials and Methods

Adeno-associated virus of serotype 5 containing a Camk2α-HA-hM4D(Gi)-IRES-mCitrine cassette provided by Dr. Bryan Roth (University of North Carolina) were obtained from UNC Vector Core at a concentration of $8 \times 10^{12}$ infectious units (IU)/ml. For control experiments a similar virus was injected expressing the optogenetic silencer ArchT instead of the chemical-genetic silencer hM4Di (AAV5-Camk2α-ArchT-GFP).

Stereotactic surgery. Animal experiments were conducted in accordance with the Animals (Scientific Procedures) Act 1986. Male Sprague-Dawley rats (6-12 weeks old, 263-325 g) were anesthetized using isoflurane and placed in a sterotaxic frame (Kopf, C A). 1.5 µl hM4Diexpressing AAV5-virus was injected at a speed of 100 nl/min into layer 5 of the forelimb area of right primary motor cortex (coordinates, 2.2-2.4 mm lateral and 1.0 mm anterior of bregma at a depth of 1.0 mm from pia; in some rats half of the volume each was deposited at 1.1 and at 0.7 mm from pia). An EEG transmitter (A3019D, Open Source Instruments (13)) was implanted subcutaneously with a subdural intracranial recording electrode positioned above the injection site. A reference electrode was implanted in the contralateral skull. For sequential injections of chemoconvulsants a Teflon cannula guide (C313GT/SP, PlasticsOne) was implanted above the injection site. For chronic epilepsy experiments, 12-16 ng of tetanus toxin (gift of Dr G. Schiavo) was injected together with hM4Di-expressing AAV5 virus in a final volume of 1.6-1.8 µl. Animals were housed separately in Faraday cages and EEG recorded continuously for up to 8 weeks post-surgery.

Seizure models. Pilocarpine (5 M in sterile saline) or picrotoxin (10 mM in 10% DMSO/sterile saline) were injected through the previously implanted Teflon cannula guide 17-52 days after hM4Di AAV injection. The volume injected was adjusted between 200 and 900 nl for pilocarpine and 100-600 nl for picrotoxin, guided by the severity of the resulting seizures in each animal, and were kept constant between matched CNO and vehicle trials. CNO (1 mg/kg, diluted 1 mg/ml in 1% DMSO/saline vehicle) or vehicle alone were injected intraperitoneally immediately after convulsant infusion. Spike-waves developed within 5 minutes of chemoconvulsant injection.

Epilepsy model. TeTx (12-16 ng) injected in a suspension with the hM4Di-expressing virus (see above), evoked high-frequency (70-160 Hz) events typically lasting less than 1 second, starting within 4 days. Such events occurred for at least 8 weeks after injection, but their frequency varied from day to day, and also depending on the time of day. Therefore, pairs of CNO-/vehicle trials were matched according to time of day, and we set a criterion that at least 2 events per hour had to occur on average over the 4 hours before the first CNO or vehicle injections for the trial to be included in the dataset. The order of CNO and matched vehicle trials was randomized. Vehicle (1% DMSO/saline) or CNO (1 mg/kg in DMSO/saline) was injected twice at 2-hour intervals, and periods lasting 3.5 hours after the first injection were analyzed.

EEG analysis. EEG was recorded and processed using the Neuroarchiver tool (Open Source Instruments) and IgorPro (Wavemetrics, Inc). The trace was centered around 0 V by subtraction of the average. Short (<100 ms), high-amplitude artifacts ("glitches") detected by threshold and periods with failed transmission were removed. The Igor script "UnipolarPeakAreas.ipf" was used to detect individual negative deflections (spike-waves), and custom-written scripts in Igor extracted their frequency as well as the coastline and power of the trace. The coastline was determined as the sum of the absolute difference between successive points. EEG epochs were also exported into Labview (National Instruments) to compute Morlet wavelet power spectra.

To establish a correlation between different types of EEG-patterns and behavior, we compared continuous video recordings with EEG traces. Simple or complex spike-waves were counted individually (by deflection), but episodes of continuous and coherent intermediate frequency activity were counted as one event per episode. We graded motor seizures on a severity scale as follows: 0 (no obvious motor seizure), 1 (contralateral forelimb twitches), 2 (repetitive shaking of forelimb, head or body), 3 (whole body shaking, arching and rearing sometimes accompanied by walking backwards).

Automated epileptiform event counting. For tetanus toxin-induced epileptic events, event sorting is explained in ref. (7). A more complete description of the seizure detection algorithm with source code is available at: http://www.opensourceinstruments.com/Electronics/A3018/Seizure_Detection.html#Similarity%20of%20Events. Intermediate-frequency (IF) oscillations evoked by picrotoxin or pilocarpine were detected by using the fast-Fourier transform of 3-second EEG segments in the range 5-14 Hz (see also FIG. 1d). The 3-second window was moved along the trace in 1-second steps. IF events were defined as periods where the peak magnitude between 5-14 Hz exceeded a threshold of 20-45 mV, depending on the overall intensity of activity. Thresholds were kept constant within each matched pair of CNO/vehicle trials.

Statistical analysis Paired t-tests or Wlcoxon tests were performed as appropriate using SPSS 20 (IBM). For seizure models, experimental time was divided up into 10-minute periods including the 10 minutes before injection as well as seven consecutive 10-minute periods after injection.

Fluorescence and immunohistochemical analysis. Brains were removed and left in 4% PFA/PBS for 3-7 days at 4° C. and then washed in PBS. Coronal slices (50 and 100 μm thickness) were cut on a vibrating slicer and examined for native mCitrine-expression right after slicing for each rat contributing to the data-set. Some of the 50 μm slices were processed further: They were permeabilized in PBS, 0.15% Triton X-100 for 20 minutes, blocked with 10% horse serum (Vector Labs) for 1 hour on a shaker, and incubated for 2 days in primary antibodies against CaMKIIα (rabbit, 1:500, Epitomics/Abcam,) and hemagglutinin (HA; mouse, 1:1000, Covance). Following three further washes in PBS (10 min), the sections were incubated in secondary antibodies (1:500, Invitrogen, labeled with Alexa-488, and Alexa-546) overnight at 4° C., washed in PBS again (4 times, 10 min) and mounted in Vectashield (Vector Labs). Images were obtained with a confocal microscope at 25× magnification of the objective and 3× digital magnification.

Results

Chemical-Genetic Silencing of Pilocarpine-Induced Acute Seizures

To test the ability of the DREADD to modify seizure activity, we injected an adenoassociated virus encoding hM4Di under the Camk2a promoter (AAV5-CaMKIIa-HA-hM4D(Gi)IRES-mCitrine) into the forelimb area of primary motor cortex (M1) of 263-325 g rats under isoflurane anaesthesia. At the same time we implanted a Teflon cannula guide (Plastics1) above the injection site to allow administration of chemoconvulsants, and a subcutaneous transmitter (Open Source Instruments, Inc.) with the active lead overlying M1 for wireless EEG recording. The transmitter samples the EEG at 512 Hz continuously for several weeks (13). Expression of hM4Di (FIG. 4) had no noticeable effects on behavior or limb use, and was confirmed by fluorescence microscopy for all rats sacrificed after 3-20 weeks.

We first examined seizures acutely evoked by chemoconvulsant injection into layer 5 of the motor cortex 17-52 days after hM4Di AAV injection. Pilocarpine (200-900 nl, 5 M) injected via the implanted cannula guide (1.6-2.0 mm from pia) elicited large-amplitude spike-wave deflections at a frequency between 0.5 and 2 Hz, starting within 5 minutes of injection and lasting between 45 and 90 minutes (FIG. 1a,b). Spike-wave complexes either had a single negative peak ('simple' spikes, SS) or featured one or more shoulders (polyspike-waves or 'complex' spikes, CS; FIG. 1b). They were interspersed with runs of intermediate frequency (IF) discharges (5-12 Hz) lasting 0.2-12 seconds, which typically had a smaller amplitude (FIG. 1b). IF discharges correlated with motor seizures at the higher end of a severity scale. This ranged from brief motor convulsions (severity score 0), through twitching of head or body (score 1), repetitive head or body shaking (score 2), to rearing, retrograde locomotion and generalized convulsions (score 3) (FIG. 1c). We therefore used the EEG power in an overlapping frequency band (4-14 Hz) as a surrogate marker to assess the anti-seizure effect of hM4Diactivation.

We randomly interleaved experiments on alternate days where either CNO (1 mg/kg in DMSO/saline vehicle) (12), or vehicle alone, was administered by intraperitoneal injection immediately after focal neocortical pilocarpine infusion. In CNO trials, both electrographic and motor convulsions were substantially reduced (14 pairs of trials in 6 rats). Paired t-tests comparing either the mean frequency of negative deflections in the EEG, the mean 4-14 Hz power, or the number of IF runs that correlate with severe motor seizures (FIG. 1c), revealed a significant decrease for a majority of the consecutive 10-min bins used to analyze data (FIG. 1e, f).

Chemical-Genetic Silencing of Picrotoxin-Induced Acute Seizures

CNO thus profoundly suppressed pilocarpine-triggered seizures. However, the interpretation of this anti-seizure effect is potentially confounded by an overlap of downstream signaling cascades of pilocarpine acting on muscarinic receptors and CNO acting on hM4Di (14). We therefore tested a second chemoconvulsant, the GABAA receptor blocker picrotoxin. Picrotoxin injection into the primary motor cortex (100-600 nl, 10 mM) also elicited electrographic and motor seizures. Those were similar in overall duration, composition of spike-wave and IF complexes, and behavioral correlates (FIG. 2a-c) to seizures caused by pilocarpine. Among minor differences, electrographic bursting switched on and off more abruptly and "complex spikes" could feature multiple (2-6) spikes succeeding at high frequency (FIG. 2b). When CNO was administered by intraperitoneal injection immediately after focal picrotoxin the electrographic discharges were again attenuated (FIG. 2e, f; 12 pairs of trials in 5 rats). This was especially marked for IF activity (FIG. 2f), which correlated with more severe motor seizures (FIG. 2c).

We asked whether off-target effects of CNO independent of hM4Di could account for its anti-seizure effect. Rats injected with an analogous virus expressing the optogenetic actuator ArchT instead of hM4Di underwent the same experimental protocol as described above, using local intracortical injection of either pilocarpine (12 pairs of trials, 6 rats) or picrotoxin (9 pairs of trials, 5 rats). We observed no significant differences between vehicle and CNO trials in any of the three measures of seizure severity.

Chemical-Genetic Silencing of Focal Neocortical Epilepsy Induced by Tetanus Toxin hM4Di activation with CNO is thus effective in two chemoconvulsant models. Does it also suppress spontaneous seizures in established epilepsy? We turned to the tetanus toxin model of chronic epilepsy (15, 16), which responds poorly to antiepileptic drugs and resembles human epilepsia partialis continua (17). This model is characterized by several EEG features, including increased high-frequency (120-160 Hz) power, increased coastline (cumulative difference between successive points on the EEG), and the occurrence of brief bursts of high-frequency EEG activity that can be detected by an automated event classifier (7) (FIG. 3a). (We limited the tetanus toxin dose for animal welfare considerations, and so motor seizures rarely occurred during the acute experiment.)

Although the half-life of CNO in rats has not been measured systematically it affects neurons transduced with hM4Di or its excitatory analog hM4Dq for at least 90 minutes (12, 18, 19), and is fully cleared within 12 hours of administration of its precursor clozapine (20). We therefore assessed electrographic markers of epilepsy during a 3.5 hour window starting with the first of two intraperitoneal injections of either CNO or vehicle, with the second injection at 2 hours. The assessment was then repeated 24 hours later, switching vehicle and CNO, to allow for washout of the agonist, and to control for diurnal variability in seizure frequency (FIG. 3b-d, 15 pairs of trials in 6 rats). All three measures of epilepsy (frequency of epileptiform bursts, coastline, and high-frequency power) were significantly attenuated by CNO when compared with vehicle (P=0.028, Wlcoxon test; n=6).

Discussion

This study shows that chemical-genetics can be used to attenuate seizures on demand. Transduction with hM4Di has no effect on neuronal excitability in the absence of its specific ligand CNO (10-12), and so this approach avoids the theoretical risk of gene therapies designed around permanent overexpression of ion channels, neurotransmitter receptors or neuropeptides. Its temporal specificity does not match that of optogenetics (refs (7-9)) because the duration of effect is dictated by the half-life of CNO, which has been estimated in humans at 7-8 hours (21). However, chemical-genetics avoids the need for invasive and biocompatible devices to deliver light to the transduced brain area close to the seizure focus. Moreover, a relatively large area may be targeted, which is not limited by absorption of light. Instead, CNO can be administered systemically.

We observed a significant reduction in seizure severity within 10 minutes of CNO administration (FIG. 1e, 2e), well below the 30-minute time-point that usually defines status epilepticus. Many patients with drug-resistant epilepsy have seizures that are preceded by premonitory auras, cluster or occur during predictable times (e.g. catamenial epilepsy), and hence might benefit from such chemical-genetic silencing.

A further potential application of chemical-genetics to epilepsy is to test the hypothesis that continued alteration of neuronal excitability for a fixed period might 'reset' epileptogenic circuits in some circumstances, bringing about a persistent reduction in seizures that outlasts the administration of the ligand. The reversibility, together with the regional and cell-type specificity of chemical genetics, distinguishes this approach from available small molecules or gene therapies based on expression of ion channels or other signalling molecules.

In conclusion, we have shown that chemical-genetics can achieve region- and cell-type specific attenuation of neuronal excitability in order to suppress seizures.

| Sequence Annex |
|---|
| Genebank file corresponding to FIG. 5 (map of viral (AAV) vector in (plasmid: 5421-8155 bp) used to deliver hM4Di): |

| | |
|---|---|
| LOCUS | pAAV_CaMKIIa_HA_ 8157 bp ds-DNA circular 28- |
| COMMENT | ApEinfo: methylated: 1 |

| FEATURES | Location/Qualifiers |
|---|---|
| misc_feature | 4286 . . . 4873<br>/vntifkey = "21"<br>/label = WPRE |
| misc_feature | 4902 . . . 5380<br>/vntifkey = "21"<br>/label = hGH\PolyA |
| misc_feature | 156 . . . 1448<br>/vntifkey = "21"<br>/label = CAMKIIa\(3.1) |
| misc_feature | 1 . . . 141<br>/vntifkey = "21"<br>/label = L-ITR |
| misc_feature | 5420 . . . 5560<br>/vntifkey = "21"<br>/label = R-ITR |
| misc_feature | 5652 . . . 5958<br>/vntifkey = "21"<br>/label = F1\Origin |
| misc_feature | 6477 . . . 7334<br>/vntifkey = "21"<br>/label = AmpR |
| misc_feature | 7485 . . . 8155<br>/vntifkey = "21"<br>/label = pUC\Ori |
| misc_feature | 1469 . . . 4259<br>/vntifkey = "21"<br>/label = HA-hM4D-IRES-mCitrine |

-continued

| Sequence Annex |
|---|

ORIGIN

```
   1 cctgcaggca gctgcgcgct cgctcgctca ctgaggccgc ccgggcaaag cccgggcgtc
  61 gggcgacctt tggtcgcccg gcctcagtga gcgagcgagc gcgcagagag ggagtggcca
 121 actccatcac tagggggttcc tgcggccgca cgcgtttaac attatggcct taggtcactt
 181 catctccatg gggttcttct tctgattttc tagaaaatga gatgggggtg cagagagctt
 241 cctcagtgac ctgcccaggg tcacatcaga aatgtcagag ctagaacttg aactcagatt
 301 actaatctta aattccatgc cttgggggca tgcaagtacg atatacagaa ggagtgaact
 361 cattagggca gatgaccaat gagtttagga aagaagagtc cagggcaggg tacatctaca
 421 ccacccgccc agccctgggt gagtccagcc acgttcacct cattatagtt gcctctctcc
 481 agtcctacct tgacgggaag cacaagcaga aactgggaca ggagcccag gagaccaaat
 541 cttcatggtc cctctgggag gatgggtggg gagagctgtg gcagaggcct caggaggggc
 601 cctgctgctc agtggtgaca gatagggggtg agaaagcaga cagagtcatt ccgtcagcat
 661 tctgggtctg tttggtactt cttctcacgc taaggtggcg gtgtgatatg cacaatggct
 721 aaaaagcagg gagagctgga agaaacaag gacagagaca gaggccaagt caaccagacc
 781 aattcccaga ggaagcaaag aaaccattac agagactaca agggggaagg gaaggagaga
 841 tgaattagct tcccctgtaa accttagaac ccagctgttg ccagggcaac ggggcaatac
 901 ctgtctcttc agaggagatg aagttgccag ggtaactaca tcctgtcttt ctcaaggacc
 961 atcccagaat gtggcaccca ctagccgtta ccatagcaac tgcctctttg ccccacttaa
1021 tcccatcccg tctgttaaaa gggccctata gttggaggtg gggaggtag aagagcgat
1081 gatcacttgt ggactaagtt tgttcgcatc cccttctcca accccctcag tacatcaccc
1141 tgggggaaca gggtccactt gctcctgggc ccacacagtc ctgcagtatt gtgtatataa
1201 ggccagggca aagaggagca ggttttaaag tgaaaggcag gcaggtgttg gggaggcagt
1261 taccggggca acgggaacag ggcgtttcgg aggtggttgc catggggacc tggatgctga
1321 cgaaggctcg cgaggctgtg agcagccaca gtgccctgct cagaagcccc aagctcgtca
1381 gtcaagccgg ttctccgttt gcactcagga gcacgggcag gcgagtggcc cctagttctg
1441 ggggcagctc tagagcggta ccggatccgc caccatgtac ccatacgatg ttccagatta
1501 cgctatggcc aacttcacac ctgtcaatgg cagctcgggc aatcagtccg tgcgcctggt
1561 cacgtcatca tcccacaatc gctatgagac ggtggaaatg gtcttcattg ccacagtgac
1621 aggctccctg agcctggtga ctgtcgtggg caacatcctg gtgatgctgt ccatcaaggt
1681 caacaggcag ctgcagacag tcaacaacta cttcctcttc agcctggcgt gtgctgatct
1741 catcataggc gccttctcca tgaacctcta caccgtgtac atcatcaagg gctactggcc
1801 cctgggcgcc gtggtctgcg acctgtggct ggccctggac tgcgtggtga gcaacgcctc
1861 cgtcatgaac cttctcatca tcagctttga ccgctacttc tgcgtcacca agcctctcac
1921 ctaccctgcc cggcgcacca ccaagatggc aggcctcatg attgctgctg cctgggtact
1981 gtccttcgtg ctctgggcgc ctgccatctt gttctggcag tttgtggtgg gtaagcggac
2041 ggtgcccgac aaccagtgct tcatccagtt cctgtccaac ccagcagtga cctttggcac
2101 agccattgct ggcttctacc tgcctgtggt catcatgacg gtgctgtaca tccacatctc
2161 cctggccagt cgcagccgag tccacaagca ccggcccgag ggcccgaagg agaagaaagc
2221 caagacgctg gccttcctca agagcccact aatgaagcag agcgtcaaga agcccccgcc
```

```
2281  cggggaggcc gcccgggagg agctgcgcaa tggcaagctg gaggaggccc ccccgccagc
2341  gctgccaccg ccaccgcgcc ccgtggctga taaggacact tccaatgagt ccagctcagg
2401  cagtgccacc cagaacacca aggaacgccc agccacagag ctgtccacca cagaggccac
2461  cacgcccgcc atgcccgccc ctcccctgca gccgcgggcc ctcaacccag cctccagatg
2521  gtccaagatc cagattgtga cgaagcagac aggcaatgag tgtgtgacag ccattgagat
2581  tgtgcctgcc acgccggctg gcatgcgccc tgcggccaac gtggcccgca agttcgccag
2641  catcgctcgc aaccaggtgc gcaagaagcg gcagatggcg gcccgggagc gcaaagtgac
2701  acgaacgatc tttgccattc tgcttgcctt catcctcacc tggacgccct acaacgtcat
2761  ggtcctggtg aacaccttct gccagagctg catccctgac acggtgtggt ccattggcta
2821  ctggctctgc tacgtcaaca gcaccatcaa ccctgcctgc tatgctctgt gcaacgccac
2881  ctttaaaaag accttccggc acctgctgct gtgccagtat cggaacatcg gcactgccag
2941  gtaggcggcc gcgatatcgc ccctctccct cccccccccc taacgttact ggccgaagcc
3001  gcttggaata aggccggtgt gcgtttgtct atatgttatt ttccaccata ttgccgtctt
3061  ttggcaatgt gagggcccgg aaacctggcc ctgtcttctt gacgagcatt cctaggggtc
3121  tttcccctct cgccaaagga atgcaaggtc tgttgaatgt cgtgaaggaa gcagttcctc
3181  tggaagcttc ttgaagacaa acaacgtctg tagcgaccct ttgcaggcag cggaaccccc
3241  cacctggcga caggtgcctc tgcggccaaa agccacgtgt ataagataca cctgcaaagg
3301  cggcacaacc ccagtgccac gttgtgagtt ggatagttgt ggaaagagtc aaatggctct
3361  cctcaagcgt attcaacaag gggctgaagg atgcccagaa ggtaccccat tgtatgggat
3421  ctgatctggg gcctcggtgc acatgcttta catgtgttta gtcgaggtta aaaaaacgtc
3481  taggcccccc gaaccacggg gacgtggttt cctttgaaaa acacgatga taagccacca
3541  tggtgagcaa gggcgaggag ctgttcaccg gggtggtgcc catcctggtc gagctggacg
3601  gcgacgtaaa cggccacaag ttcagcgtgt ccggcgaggg cgagggcgat gccacctacg
3661  gcaagctgac cctgaagttc atctgcacca ccggcaagct gcccgtgccc tggcccaccc
3721  tcgtgaccac cttcggctac ggcctgatgt gcttcgcccg ctaccccgac cacatgaagc
3781  agcacgactt cttcaagtcc gccatgcccg aaggctacgt ccaggagcgc accatcttct
3841  tcaaggacga cggcaactac aagacccgcg ccgaggtgaa gttcgagggc gacaccctgg
3901  tgaaccgcat cgagctgaag ggcatcgact tcaaggagga cggcaacatc ctggggcaca
3961  agctggagta caactacaac agccacaacg tctatatcat ggccgacaag cagaagaacg
4021  gcatcaaggt gaacttcaag atccgccaca acatcgagga cggcagcgtg cagctcgccg
4081  accactacca gcagaacacc cccatcggcg acggccccgt gctgctgccc gacaaccact
4141  acctgagcta ccagtccaaa ctgagcaaag ccccaacga gaagcgcgat cacatggtcc
4201  tgctggagtt cgtgaccgcc gccgggatca ctctcggcat ggacgagctg tacaagtgag
4261  aattcgatat caagcttatc gataatcaac ctctggatta caaaatttgt gaaagattga
4321  ctggtattct taactatgtt gctccttta cgctatgtgg atacgctgct ttaatgcctt
4381  tgtatcatgc tattgcttcc cgtatggctt tcattttctc ctccttgtat aaatcctggt
4441  tgctgtctct ttatgaggag ttgtggcccg ttgtcaggca acgtggcgtg gtgtgcactg
4501  tgtttgctga cgcaacccc actggttggg gcattgccac cacctgtcag ctcctttccg
4561  ggactttcgc tttccccctc cctattgcca cggcggaact catcgccgcc tgccttgccc
```

```
4621  gctgctggac aggggctcgg ctgttgggca ctgacaattc cgtggtgttg tcggggaaat
4681  catcgtcctt tccttggctg ctcgcctgtg ttgccacctg gattctgcgc gggacgtcct
4741  tctgctacgt cccttcggcc ctcaatccag cggaccttcc ttcccgcggc ctgctgccgg
4801  ctctgcggcc tcttccgcgt cttcgccttc gccctcagac gagtcggatc tcccttt ggg
4861  ccgcctcccc gcatcgatac cgagcgctgc tcgagagatc tacgggtggc atccctgtga
4921  cccctcccca gtgcctctcc tggccctgga agttgccact ccagtgccca ccagccttgt
4981  cctaataaaa ttaagttgca tcattttgtc tgactaggtg tccttctata atattatggg
5041  gtggaggggg gtggtatgga gcaaggggca agttgggaag acaacctgta gggcctgcgg
5101  ggtctattgg gaaccaagct ggagtgcagt ggcacaatct ggctcactgc aatctccgc
5161  ctcctgggtt caagcgattc tcctgcctca gcctcccgag ttgttgggat tccaggcatg
5221  catgaccagg ctcagctaat ttttgttttt ttggtagaga cggggtttca ccatattggc
5281  caggctggtc tccaactcct aatctcaggt gatctaccca ccttggcctc ccaaattgct
5341  gggattacag gcgtgaacca ctgctccctt ccctgtcctt ctgattttgt aggtaaccac
5401  gtgcggaccg agcggccgca ggaacccta gtgatggagt tggccactcc ctctctgcgc
5461  gctcgctcgc tcactgaggc cgggcgacca aaggtcgccc gacgcccggg ctttgcccgg
5521  gcggcctcag tgagcgagcg agcgcgcagc tgcctgcagg ggcgcctgat gcggtatttt
5581  ctccttacgc atctgtgcgg tatttcacac cgcatacgtc aaagcaacca tagtacgcgc
5641  cctgtagcgg cgcattaagc gcggcgggtg tggtggttac gcgcagcgtg accgctacac
5701  ttgccagcgc cctagcgccc gctcctttcg ctttcttccc ttcctttctc gccacgttcg
5761  ccggctttcc ccgtcaagct ctaaatcggg ggctcccttt agggttccga tttagtgctt
5821  tacggcacct cgaccccaaa aaacttgatt tgggtgatgg ttcacgtagt gggccatcgc
5881  cctgatagac ggttttttcg ccttttgacgt tggagtccac gttctttaat agtggactct
5941  tgttccaaac tggaacaaca ctcaacccta tctcgggcta ttcttttgat ttataaggga
6001  ttttgccgat ttcggcctat tggttaaaaa atgagctgat ttaacaaaaa tttaacgcga
6061  attttaacaa atattaacg tttacaattt tatggtgcac tctcagtaca atctgctctg
6121  atgccgcata gttaagccag ccccgacacc cgccaacacc cgctgacgcg ccctgacggg
6181  cttgtctgct cccggcatcc gcttacagac aagctgtgac cgtctccggg agctgcatgt
6241  gtcagaggtt ttcaccgtca tcaccgaaac gcgcgagacg aaagggcctc gtgatacgcc
6301  tatttttata ggttaatgtc atgataataa tggtttctta gacgtcaggt ggcacttttc
6361  ggggaaatgt gcgcggaacc cctatttgtt tatttttcta aatacattca aatatgtatc
6421  cgctcatgag acaataaccc tgataaatgc ttcaataata ttgaaaaagg aagagtatga
6481  gtattcaaca tttccgtgtc gcccttattc ccttttttgc ggcatttt gc cttcctgttt
6541  ttgctcaccc agaaacgctg gtgaaagtaa aagatgctga agatcagttg ggtgcacgag
6601  tgggttacat cgaactggat ctcaacagcg gtaagatcct tgagagtttt cgccccgaag
6661  aacgttttcc aatgatgagc acttttaaag ttctgctatg tggcgcggta ttatcccgta
6721  ttgacgccgg gcaagagcaa ctcggtcgcc gcatacacta ttctcagaat gacttggttg
6781  agtactcacc agtcacagaa aagcatctta cggatggcat gacagtaaga gaattatgca
6841  gtgctgccat aaccatgagt gataacactg cggccaactt acttctgaca acgatcggag
6901  gaccgaagga gctaaccgct tttttgcaca acatggggga tcatgtaact cgccttgatc
```

-continued

Sequence Annex

```
6961  gttgggaacc ggagctgaat gaagccatac caaacgacga gcgtgacacc acgatgcctg 7021  tagcaatggc aacaacgttg cgcaaactat taactggcga actacttact ctagcttccc 7081  ggcaacaatt aatagactgg atggaggcgg ataaagttgc aggaccactt ctgcgctcgg 7141  cccttccggc tggctggttt attgctgata aatctggagc cggtgagcgt gggtctgcg 7201  gtatcattgc agcactgggg ccagatggta agccctcccg tatcgtagtt atctacacga 7261  cggggagtca ggcaactatg gatgaacgaa atagacagat cgctgagata ggtgcctcac 7321  tgattaagca ttggtaactg tcagaccaag tttactcata tatactttag attgatttaa 7381  aacttcattt ttaatttaaa aggatctagg tgaagatcct ttttgataat ctcatgacca 7441  aaatcccta acgtgagttt tcgttccact gagcgtcaga ccccgtagaa aagatcaaag 7501  gatcttcttg agatccttt tttctgcgcg taatctgctg cttgcaaaca aaaaaccac 7561  cgctaccagc ggtggtttgt ttgccggatc aagagctacc aactcttttt ccgaaggtaa 7621  ctggcttcag cagagcgcag ataccaaata ctgtccttct agtgtagccg tagttaggcc 7681  accacttcaa gaactctgta gcaccgccta catacctcgc tctgctaatc ctgttaccag 7741  tggctgctgc cagtggcgat aagtcgtgtc ttaccgggtt ggactcaaga cgatagttac 7801  cggataaggc gcagcggtcg ggctgaacgg ggggttcgtg cacacagccc agcttggagc 7861  gaacgaccta caccgaactg agatacctac agcgtgagct atgagaaagc gccacgcttc 7921  ccgaagggag aaaggcggac aggtatccgg taagcggcag ggtcggaaca ggagagcgca 7981  cgagggagct tccaggggga aacgcctggt atctttatag tcctgtcggg tttcgccacc 8041  tctgacttga gcgtcgattt ttgtgatgct cgtcaggggg gcggagccta tggaaaaacg 8101  ccagcaacgc ggccttttta cggttcctgg cctttgctg gccttttgct
      cacatgt
//
```

REFERENCES

1 A. K. Ngugi, C. Bottomley, I. Kleinschmidt, J. W. Sander, C. R. Newton, Estimation of the burden of active and life-time epilepsy: a meta-analytic approach, *Epilepsia* 51, 883-890 (2010).

2 P. Kwan, S. C. Schachter, M. J. Brodie, Drug-resistant epilepsy, *N. Engl. J. Med.* 365, 919-926 (2011).

3 J. F. Annegers, W. A. Hauser, L. R. Elveback, Remission of seizures and relapse in patients with epilepsy, *Epilepsia* 20, 729-737 (1979).

4 F. Rosenow, H. Lüders, Presurgical evaluation of epilepsy, *Brain J. Neurol.* 124, 1683-1700 (2001).

5 S. U. Schuele, H. O. Lüders, Intractable epilepsy: management and therapeutic alternatives, *Lancet Neurol.* 7, 514-524 (2008).

6 J. de Tisi et al., The long-term outcome of adult epilepsy surgery, patterns of seizure remission, and relapse: a cohort study, *Lancet* 378, 1388-1395 (2011).

7 R. C. Wykes et al., Optogenetic and potassium channel gene therapy in a rodent model of focal neocortical epilepsy, *Sci. Transl. Med.* 4, 161ra152 (2012).

8 J. T. Paz et al., Closed-loop optogenetic control of thalamus as a tool for interrupting seizures after cortical injury, *Nat. Neurosci.* 16, 64-70 (2013).

9 E. Krook-Magnuson, C. Armstrong, M. Oijala, I. Soltesz, On-demand optogenetic control of spontaneous seizures in temporal lobe epilepsy, *Nat. Commun.* 4, 1376 (2013).

10 Y. Pei, S. C. Rogan, F. Yan, B. L. Roth, Engineered GPCRs as tools to modulate signal transduction, *Physiol. Bethesda Md.* 23, 313-321 (2008).

11 B. N. Armbruster, X. Li, M. H. Pausch, S. Herlitze, B. L. Roth, Evolving the lock to fit the key to create a family of G protein-coupled receptors potently activated by an inert ligand, *Proc. Natl. Acad. Sci. U.S.A.* 104, 5163-5168 (2007).

12 S. M. Ferguson et al., Transient neuronal inhibition reveals opposing roles of indirect and direct pathways in sensitization, *Nat. Neurosci.* 14, 22-24 (2011).

13 P. Chang, K. S. Hashemi, M. C. Walker, A novel telemetry system for recording EEG in small animals, *J. Neurosci. Methods* 201, 106-115 (2011).

14 P. Wulff, B. R. Arenkiel, Chemical genetics: receptor-ligand pairs for rapid manipulation of neuronal activity, *Curr. Opin. Neurobiol.* 22, 54-60 (2012).

15 E. D. Louis, P. D. Williamson, T. M. Darcey, Chronic focal epilepsy induced by microinjection of tetanus toxin into the cat motor cortex, *Electroencephalogr. Clin. Neurophysiol.* 75, 548-557 (1990).

16 K. E. Nilsen, M. C. Walker, H. R. Cock, Characterization of the tetanus toxin model of refractory focal neocortical epilepsy in the rat, *Epilepsia* 46, 179-187 (2005).

17 O. C. Cockerell, J. Rothwell, P. D. Thompson, C. D. Marsden, S. D. Shorvon, Clinical and physiological features of epilepsia partialis continua. Cases ascertained in the UK, *Brain J. Neurol.* 119 (Pt 2), 393-407 (1996).

18 A. R. Garner et al., Generation of a synthetic memory trace, *Science* 335, 1513-1516 (2012).
19 G. M. Alexander et al., Remote control of neuronal activity in transgenic mice expressing evolved G protein-coupled receptors, *Neuron* 63, 27-39 (2009).
20 R. J. Baldessarini et al., Tissue Concentrations of Clozapine and its Metabolites in the Rat, *Neuropsychopharmacology* 9, 117-124 (1993).
21 C. Guitton, M. Abbar, J. M. Kinowski, P. Chabrand, F. Bressolle, Multiple-dose pharmacokinetics of clozapine in patients with chronic schizophrenia, *J. Clin. Psychopharmacol.* 18, 470-476 (1998).
22 M. J. Cook et al., Prediction of seizure likelihood with a long-term, implanted seizure advisory system in patients with drug-resistant epilepsy: a first-in-man study, *Lancet Neurol.* 12, 563-571 (2013).
23 R. Hovorka, Closed-loop insulin delivery: from bench to clinical practice, *Nat. Rev. Endocrinol.* 7, 385-395 (2011).
24 Majeed Z R, Nichols C D, Cooper R L. 5-HT stimulation of heart rate in Drosophila does not act through cAMP as revealed by pharmacogenetics. *J Appl Physiol.* December; 115(11):1656-65 (2013).
25 Shah V N, Shoskes A, Tawfik B, Garg S K. Closed-loop system in the management of diabetes: past, present, and future. *Diabetes Technol Ther.* August; 16(8):477-90 (2014).
26 Kätzel D, Nicholson E, Schorge S, Walker M C, Kullmann D M. Chemical-genetic attenuation of focal neocortical seizures. *Nat Commun.* May 27; 5:3847. doi: 10.1038/ncomms4847 (2014).
27 Chen et al "The First Structure-Activity Relationship Studies for Designer Receptors Exclusively Activated by Designer Drugs". ACS Chem Neurosci. 2015 Jan. 27

The invention claimed is:

1. A method of treating a seizure disorder, which is focal epilepsy, in a patient suffering from said disorder,
wherein either
(a) said patient has previously been administered a vector encoding a modified receptor,
wherein the modified receptor is a human muscarinic acetylcholine receptor M4, which is a Gi protein-coupled receptor (GPCR), coupled via a Gi-protein to a G protein-coupled inwardly rectifying potassium channel (GIRK), and
wherein the modified receptor is characterised by (i) a decreased responsiveness to its endogenous activating ligand and/or (ii) a retained or enhanced responsiveness to an exogenous agonist, or
(b) administering to the patient said vector,
wherein the modified receptor is encoded by a nucleic acid operably linked to a neuronal cell type-specific promoter such that said modified receptor is expressed in excitatory neurons of a seizure focus in brain of the patient;

which method comprises subsequently administering to said patient said exogenous agonist wherein the exogenous agonist is olanzapine, whereby the presence of said agonist in the brain of the patient activates said modified receptor, whereby activation of said modified receptor reversibly inhibits the excitability of, and neurotransmission by, the excitatory neurons in the seizure focus.

2. The method of claim 1, wherein the exogenous ligand is administered within 30 minutes before or 24 hours after the human has an epileptic seizure.

3. The method of claim 1, wherein the exogenous ligand is administered prior to the patient having an epileptic seizure or during an epileptic seizure.

4. The method of claim 3, wherein the exogenous ligand is administered automatically either (i) by a device that is either coupled to an automated seizure detection mechanism, or (ii) in response to a predicted seizure by EEG analysis.

* * * * *

SEQUENCE LISTING

```
<160> NUMBER OF SEQ ID NOS: 1

<210> SEQ ID NO 1
<211> LENGTH: 8157
<212> TYPE: DNA
<213> ORGANISM: Artificial sequence
<220> FEATURE:
<223> OTHER INFORMATION: Synthetic sequence: Plasmid
      pAAV5-CaMKIIa-HAhM4D(Gi)-IRES-mCitrine UNC encoding AAV5 virus
      expressing hM4Di sequence

<400> SEQUENCE: 1
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgca cgcgtttaac attatggcct taggtcactt     180
catctccatg gggttcttct tctgattttc tagaaaatga gatgggggtg cagagagctt     240
cctcagtgac ctgcccaggg tcacatcaga aatgtcagag ctagaacttg aactcagatt     300
actaatctta aattccatgc cttggggca tgcaagtacg atatacagaa ggagtgaact     360
cattagggca gatgaccaat gagtttagga aagaagagtc cagggcaggg tacatctaca     420
ccacccgccc agccctgggt gagtccagcc acgttcacct cattatagtt gcctctctcc     480
agtcctacct tgacgggaag cacaagcaga aactgggaca ggagcccccag gagaccaaat     540 cttcatggtc cctctgggag gatgggtggg gagagctgtg gcagaggcct caggaggggc     600
cctgctgctc agtggtgaca gatagggtg agaaagcaga cagagtcatt ccgtcagcat     660
tctgggtctg tttggtactt cttctcacgc taaggtggcg gtgtgatatg cacaatggct     720
aaaaagcagg gagagctgga aagaaacaag gacagagaca gaggccaagt caaccagacc     780
aattcccaga ggaagcaaag aaaccattac agagactaca aggggaagg gaaggagaga     840 tgaattagct tcccctgtaa accttagaac ccagctgttg ccagggcaac ggggcaatac     900
ctgtctcttc agaggagatg aagttgccag ggtaactaca tcctgtcttt ctcaaggacc     960
atcccagaat gtggcaccca ctagccgtta ccatagcaac tgcctctttg ccccacttaa    1020
tcccatcccg tctgttaaaa gggccctata gttggaggtg ggggaggtag gaagagcgat    1080
gatcacttgt ggactaagtt tgttcgcatc cccttctcca accccctcag tacatcaccc    1140
tgggggaaca gggtccactt gctcctgggc ccacacagtc ctgcagtatt gtgtatataa    1200
ggccagggca aagaggagca ggttttaaag tgaaaggcag gcaggtgttg gggaggcagt    1260
taccggggca acgggaacag ggcgtttcgg aggtggttgc catggggacc tggatgctga    1320
```

```
cgaaggctcg cgaggctgtg agcagccaca gtgccctgct cagaagcccc aagctcgtca    1380
gtcaagccgg ttctccgttt gcactcagga gcacgggcag gcgagtggcc cctagttctg    1440
ggggcagctc tagagcggta ccggatccgc caccatgtac ccatacgatg ttccagatta    1500
cgctatggcc aacttcacac tgtcaatgg cagctcgggc aatcagtccg tgcgcctggt    1560
cacgtcatca tcccacaatc gctatgagac ggtggaaatg gtcttcattg ccacagtgac    1620
aggctccctg agcctggtga ctgtcgtggg caacatcctg gtgatgctgt ccatcaaggt    1680
caacaggcag ctgcagacag tcaacaacta cttcctcttc agcctggcgt gtgctgatct    1740
catcataggc gccttctcca tgaacctcta caccgtgtac atcatcaagg ctactggcc    1800 cctgggcgcc gtggtctgcg acctgtggct ggccctggac tgcgtggtga gcaacgcctc    1860
cgtcatgaac cttctcatca tcagctttga ccgctacttc tgcgtcacca gcctctcac    1920 ctaccctgcc cggcgcacca ccaagatggc aggcctcatg attgctgctg cctgggtact    1980
gtccttcgtg ctctgggcgc tgccatctt gttctggcag tttgtggtgg gtaagcggac    2040
ggtgcccgac aaccagtgct tcatccagtt cctgtccaac ccagcagtga cctttggcac    2100
agccattgct ggcttctacc tgcctgtggt catcatgacg gtgctgtaca tccacatctc    2160
cctggccagt cgcagccgag tccacaagca ccggcccgag ggcccgaagg agaagaaagc    2220
caagacgctg gccttcctca agagcccact aatgaagcag agcgtcaaga gccccccgcc    2280
cggggaggcc gcccgggagg agctgcgcaa tggcaagctg gaggagcccc cccgccagc    2340 gctgccaccg ccaccgcgcc ccgtggctga taaggacact tccaatgagt ccagctcagg    2400
cagtgccacc cagaacacca aggaacgccc agccacagag ctgtccacca cagaggccac    2460
cacgcccgcc atgcccgccc tcccctgca gccgcgggcc ctcaaccag cctccagatg    2520 gtccaagatc cagattgtga cgaagcagac aggcaatgag tgtgtgacag ccattgagat    2580
tgtgcctgcc acgccggctg gcatgcgccc tgcggccaac gtggcccgca gttcgccag    2640 catcgctcgc aaccaggtgc gcaagaagcg gcagatggcg gcccgggagc gcaaagtgac    2700
acgaacgatc tttgccattc tgcttgcctt catcctcacc tggacgccct acaacgtcat    2760
ggtcctggtg aacaccttct gccagagctg catccctgac acggtgtggt ccattggcta    2820
ctggctctgc tacgtcaaca gcaccatcaa ccctgcctgc tatgctctgt gcaacgccac    2880
ctttaaaaag accttccggc acctgctgct gtgccagtat cggaacatcg gcactgccag    2940
gtaggcggcc gcgatatcgc ccctctccct cccccccccc taacgttact ggccgaagcc    3000
gcttggaata aggccggtgt gcgttttgtct atatgttatt ttccaccata ttgccgtctt    3060
ttggcaatgt gagggcccgg aaacctggcc ctgtcttctt gacgagcatt cctagggtc    3120 tttccctct cgccaaagga atgcaaggtc tgttgaatgt cgtgaaggaa gcagttcctc    3180
tggaagcttc ttgaagacaa acaacgtctg tagcgaccct ttgcaggcag cggaaccccc    3240
cacctggcga caggtgcctc tgcggccaaa agccacgtgt ataagataca cctgcaaagg    3300
cggcacaacc ccagtgccac gttgtgagtt ggatagttgt ggaaagagtc aaatggctct    3360
cctcaagcgt attcaacaag gggctgaagg atgcccagaa ggtaccccat tgtatgggat    3420
ctgatctggg gcctcggtgc acatgcttta catgtgttta gtcgaggtta aaaaaacgtc    3480
taggcccccc gaaccacggg gacgtggttt tcctttgaaa aacacgatga taagccacca    3540
tggtgagcaa gggcgaggag ctgttcaccg gggtggtgcc catcctggtc gagctggacg    3600
gcgacgtaaa cggccacaag ttcagcgtgt ccggcgaggg cgaggcgat gccacctacg    3660 gcaagctgac cctgaagttc atctgcacca ccggcaagct gcccgtgccc tggcccaccc    3720
```

```
tcgtgaccac cttcggctac ggcctgatgt gcttcgcccg ctaccccgac cacatgaagc    3780
agcacgactt cttcaagtcc gccatgcccg aaggctacgt ccaggagcgc accatcttct    3840
tcaaggacga cggcaactac aagacccgcg ccgaggtgaa gttcgagggc gacaccctgg    3900
tgaaccgcat cgagctgaag ggcatcgact tcaaggagga cggcaacatc ctggggcaca    3960
agctggagta caactacaac agccacaacg tctatatcat ggccgacaag cagaagaacg    4020
gcatcaaggt gaacttcaag atccgccaca acatcgagga cggcagcgtg cagctcgccg    4080
accactacca gcagaacacc cccatcggcg acggccccgt gctgctgccc gacaaccact    4140
acctgagcta ccagtccaaa ctgagcaaag accccaacga gaagcgcgat cacatggtcc    4200
tgctggagtt cgtgaccgcc gccgggatca ctctcggcat ggacgagctg tacaagtgag    4260
aattcgatat caagcttatc gataatcaac ctctggatta caaaatttgt gaaagattga    4320
ctggtattct taactatgtt gctcctttta cgctatgtgg atacgctgct ttaatgcctt    4380
tgtatcatgc tattgcttcc cgtatggctt tcattttctc ctccttgtat aaatcctggt    4440
tgctgtctct ttatgaggag ttgtggcccg ttgtcaggca acgtggcgtg gtgtgcactg    4500
tgtttgctga cgcaaccccc actggttggg gcattgccac cacctgtcag ctcctttccg    4560
ggactttcgc tttccccctc cctattgcca cggcggaact catcgccgcc tgccttgccc    4620
gctgctggac aggggctcgg ctgttgggca ctgacaattc cgtggtgttg tcggggaaat    4680
catcgtcctt tccttggctg ctcgcctgtg ttgccacctg gattctgcgc gggacgtcct    4740
tctgctacgt cccttcggcc ctcaatccag cggaccttcc ttcccgcggc ctgctgccgg    4800
ctctgcggcc tcttccgcgt cttcgccttc gccctcagac gagtcggatc tccctttggg    4860
ccgcctcccc gcatcgatac cgagcgctgc tcgagagatc tacgggtggc atccctgtga    4920
cccctcccca gtgcctctcc tggccctgga agttgccact ccagtgccca ccagccttgt    4980
cctaataaaa ttaagttgca tcattttgtc tgactaggtg tccttctata atattatggg    5040
gtggaggggg gtggtatgga gcaaggggca agttgggaag acaacctgta gggcctgcgg    5100
ggtctattgg gaaccaagct ggagtgcagt ggcacaatct ggctcactg caatctccgc    5160 ctcctgggtt caagcgattc tcctgcctca gcctcccgag ttgttgggat tccaggcatg    5220
catgaccagg ctcagctaat ttttgttttt ttggtagaga cggggtttca ccatattggc    5280
caggctggtc tccaactcct aatctcaggt gatctaccca ccttggcctc ccaaattgct    5340
gggattacag gcgtgaacca ctgctccctt ccctgtcctt ctgattttgt aggtaaccac    5400
gtgcggaccg agcggccgca ggaaccccta gtgatggagt tggccactcc ctctctgcgc    5460
gctcgctcgc tcactgaggc cgggcgacca aggtcgccc gacgcccggg ctttgcccgg    5520
gcggcctcag tgagcgagcg agcgcgcagc tgcctgcagg ggcgcctgat gcggtattt    5580 ctccttacgc atctgtgcgg tatttcacac cgcatacgtc aaagcaacca tagtacgcgc    5640
cctgtagcgg cgcattaagc gcggcgggtg tggtggttac gcgcagcgtg accgctacac    5700
ttgccagcgc cctagcgccc gctccttcg ctttcttccc ttcctttctc gccacgttcg    5760
ccggctttcc ccgtcaagct ctaaatcggg ggctcccttt agggttccga tttagtgctt    5820
tacggcacct cgaccccaaa aaacttgatt tgggtgatgg ttcacgtagt gggccatcgc    5880
cctgatagac ggtttttcgc cctttgacgt tggagtccac gttctttaat agtggactct    5940
tgttccaaac tggaacaaca ctcaacccta tctcgggcta ttcttttgat ttataaggga    6000
ttttgccgat ttcggcctat tggttaaaaa atgagctgat ttaacaaaaa tttaacgcga    6060
attttaacaa aatattaacg tttacaattt tatggtgcac tctcagtaca atctgctctg    6120
```

```
atgccgcata gttaagccag ccccgacacc cgccaacacc cgctgacgcg ccctgacggg    6180
cttgtctgct cccggcatcc gcttacagac aagctgtgac cgtctccggg agctgcatgt    6240
gtcagaggtt ttcaccgtca tcaccgaaac gcgcgagacg aaagggcctc gtgatacgcc    6300
tatttttata ggttaatgtc atgataataa tggtttctta gacgtcaggt ggcacttttc    6360
ggggaaatgt gcgcggaacc cctatttgtt tattttctca aatacattca aatatgtatc    6420
cgctcatgag acaataaccc tgataaatgc ttcaataata ttgaaaaagg aagagtatga    6480
gtattcaaca tttccgtgtc gcccttattc cctttttgc ggcattttgc cttcctgttt    6540
ttgctcaccc agaaacgctg gtgaaagtaa aagatgctga agatcagttg ggtgcacgag    6600
tgggttacat cgaactggat ctcaacagcg gtaagatcct tgagagtttt cgccccgaag    6660
aacgttttcc aatgatgagc acttttaaag ttctgctatg tggcgcggta ttatcccgta    6720
ttgacgccgg gcaagagcaa ctcggtcgcc gcatacacta ttctcagaat gacttggttg    6780
agtactcacc agtcacagaa aagcatctta cggatggcat gacagtaaga gaattatgca    6840
gtgctgccat aaccatgagt gataacactg cggccaactt acttctgaca acgatcggag    6900
gaccgaagga gctaaccgct tttttgcaca acatggggga tcatgtaact cgccttgatc    6960
gttgggaacc ggagctgaat gaagccatac caaacgacga gcgtgacacc acgatgcctg    7020
tagcaatggc aacaacgttg cgcaaactat taactggcga actacttact ctagcttccc    7080
ggcaacaatt aatagactgg atggaggcgg ataaagttgc aggaccactt ctgcgctcgg    7140
cccttccggc tggctggttt attgctgata aatctggagc cggtgagcgt gggtctcgcg    7200
gtatcattgc agcactgggg ccagatggta agccctcccg tatcgtagtt atctacacga    7260
cggggagtca ggcaactatg gatgaacgaa atagacagat cgctgagata ggtgcctcac    7320
tgattaagca ttggtaactg tcagaccaag tttactcata tatactttag attgatttaa    7380
aacttcattt ttaatttaaa aggatctagg tgaagatcct ttttgataat ctcatgacca    7440
aaatccctta acgtgagttt tcgttccact gagcgtcaga ccccgtagaa aagatcaaag    7500
gatcttcttg agatcctttt tttctgcgcg taatctgctg cttgcaaaca aaaaaaccac    7560
cgctaccagc ggtggtttgt ttgccggatc aagagctacc aactctttt ccgaaggtaa    7620
ctggcttcag cagagcgcag ataccaaata ctgtccttct agtgtagccg tagttaggcc    7680
accacttcaa gaactctgta gcaccgccta catacctcgc tctgctaatc ctgttaccag    7740
tggctgctgc cagtggcgat aagtcgtgtc ttaccgggtt ggactcaaga cgatagttac    7800
cggataaggc gcagcggtcg ggctgaacgg ggggttcgtg cacacagccc agcttggagc    7860
gaacgaccta caccgaactg agatacctac agcgtgagct atgagaaagc gccacgcttc    7920
ccgaagggag aaaggcggac aggtatccgg taagcggcag ggtcggaaca ggagagcgca    7980
cgagggagct tccaggggga aacgcctggt atctttatag tcctgtcggg tttcgccacc    8040
tctgacttga gcgtcgattt ttgtgatgct cgtcaggggg gcggagccta tggaaaaacg    8100
ccagcaacgc ggccttttta cggttcctgg ccttttgctg gccttttgct cacatgt       8157
```